(12) United States Patent
Hart et al.

(10) Patent No.: US 10,617,307 B2
(45) Date of Patent: Apr. 14, 2020

(54) PATIENT MONITORING METHOD AND MONITORING DEVICE

(71) Applicants: Guy's and St. Thomas' NHS Foundation Trust, of The Counting House, Guy's Hospital, London (GB); King's College London, of The Strand, London (GB)

(72) Inventors: Nicholas Hart, London (GB); John Moxham, London (GB); Fiammetta Fedele, London (GB)

(73) Assignees: Guy's and St. Thomas' NHS Foundation Trust, of The Counting House, Guy's Hospital, London (GB); King's College London, of The Strand, London (GB)

( * ) Notice: Subject to any disclaimer, the term of this patent is extended or adjusted under 35 U.S.C. 154(b) by 214 days.

(21) Appl. No.: 15/640,049

(22) Filed: Jun. 30, 2017

(65) Prior Publication Data

US 2018/0020928 A1    Jan. 25, 2018

Related U.S. Application Data

(63) Continuation of application No. 13/627,383, filed on Sep. 26, 2012, now abandoned.
(Continued)

(30) Foreign Application Priority Data

Sep. 30, 2011    (GB) .................................. 1116860.6

(51) Int. Cl.
*A61B 5/0205*    (2006.01)
*A61B 5/04*    (2006.01)
(Continued)

(52) U.S. Cl.
CPC ........ *A61B 5/0205* (2013.01); *A61B 5/04012* (2013.01); *A61B 5/0488* (2013.01);
(Continued)

(58) Field of Classification Search
None
See application file for complete search history.

(56) References Cited

U.S. PATENT DOCUMENTS 4,686,998 A *  8/1987  Robbins ............... A61B 5/0006
                                              128/903
5,524,632 A     6/1996  Stein et al.
(Continued)

OTHER PUBLICATIONS

Murphy et al., "Neural Respiratory Drive as a Physiological Biomarker to Monitor Change During Acute Exacerbations of Chronic Obstructive Pulmonary Disease: Online Data Supplement". Published online Jun. 15, 2011. Retrieved Mar. 25, 2019 from https://thorax.bmj.com (Year: 2011).*

(Continued)

*Primary Examiner* — Matthew Kremer
*Assistant Examiner* — Samuel C Kim
(74) *Attorney, Agent, or Firm* — Bozicevic, Field & Francis LLP; Paula A. Borden

(57) ABSTRACT

A method of monitoring a patient includes measuring neural respiratory drive using a monitoring device (10), repeating the measurement either continuously or at regular time intervals, and comparing the measurements obtained in order to predict treatment failure and/or clinical deterioration and/or re-admission. In embodiments of the invention, the neural respiratory drive is measured by obtaining a measure of the second intercostal space parasternal electromyogram. A monitoring device (10) includes a signal input (20), a processing unit (30), and a output unit (50), and is arranged to measure the neural respiratory drive, store the measured (Continued)

value and compare it to a previously measured value for the neural respiratory drive.

17 Claims, 18 Drawing Sheets

Related U.S. Application Data

(60) Provisional application No. 61/541,708, filed on Sep. 30, 2011.

(51) Int. Cl.
| | |
|---|---|
| *A61B 5/08* | (2006.01) |
| *A61B 5/0488* | (2006.01) |
| *A61B 5/00* | (2006.01) |
| *A61B 5/0472* | (2006.01) |
| *A61B 5/0452* | (2006.01) |
| *A61B 5/0245* | (2006.01) |

(52) U.S. Cl.
CPC .............. *A61B 5/08* (2013.01); *A61B 5/0245* (2013.01); *A61B 5/04017* (2013.01); *A61B 5/0452* (2013.01); *A61B 5/0472* (2013.01); *A61B 5/7203* (2013.01)

(56) References Cited

U.S. PATENT DOCUMENTS

| | | | | |
|---|---|---|---|---|
| 6,588,423 | B1 | 7/2003 | Sinderby | |
| 2004/0064066 | A1* | 4/2004 | John | A61B 5/04845 600/559 |
| 2007/0118044 | A1* | 5/2007 | Remes | A61B 5/0488 600/546 |
| 2008/0188903 | A1* | 8/2008 | Tehrani | A61N 1/3601 607/42 |
| 2012/0041279 | A1* | 2/2012 | Freeman | A61B 5/0205 600/301 |

OTHER PUBLICATIONS

Jolley et al., "Neural Respiratory Drive in Healthy Subjects and in Chronic Obstructive Pulmonary Disease: Online Depository". Published online Jan. 30, 2009. Retrieved Mar. 25, 2019 from https://erj.ersjournals.com. (Year: 2009).*
Anthonisen, et al., "Antibiotic Therapy in Exacerbations of Chronic Obstructive Pulmonary Disease", Annals of Internal Medicine, 1987, vol. 106, pp. 196-204.
Standardization of Spirometry—1987 Update, Am. Rev. Respir. Dis., 1987, vol. 136, pp. 1285-1298.
Bland, et al., "Statistical Methods for Assessing Agreement Between Two Methods of Clinical Measurement", The Lancet, 1986, pp. 307-310.
Borg, "Psychophysical Bases of Perceived Exertion", Medicine and Science in Sports and Exercise, 1982, vol. 14, No. 5, pp. 377-381.
Cao, et al., "Frequent Hospital Readmissions for Acute Exacerbation of COPD and Their Associated Factors", Respirology, 2006, vol. 11, pp. 188-195.
Celli, et al., "The Body-Mass Index, Airflow Obstruction, Dyspnea, and Exercise Capacity Index in Chronic Obstructive Pulmonary Disease", The New England Journal of Medicine, 2004, vol. 350, No. 10, pp. 1005-1012.
De Troyer, et al., "On the Mechanism of the Mediolateral Gradient of Parasternal Ativation", 1996, the American Physiological Society, pp. 1490-1494.
De Troyer, "Effect of Diaphragmatic Contraction on the Action of the Canine Parasternal Intercostals", J Appl Physiol, 2006, vol. 101, pp. 169-175.
Duiverman, et al., "Reproducibility and Responsiveness of a Non-invasive EMG Technique of the Respiratory Muscles in COPD Patients and in Healthy Subjects", J Appl Physiol, 2004, vol. 96, pp. 1723-1729.
Easton, et al., "Postinspiratory Activity of the Parasternal and External Intercostal Muscles in Awake Canines", J Appl Physiol, 1999, vol. 87, pp. 1097-1101.
Gandevia, et al., "Spatial Distribution of Intercostal Muscles in Humans", J Physiol, 2006, vol. 573.1, pp. 263-275.
Garcia-Aymerich, et al., "Risk Factors of Readmission to Hospital for a COPD Exacerbation: a Prospective Study", Thorax, 2003, vol. 58, pp. 100-105.
Guyatt, et. al., "A Measure of Quality of Life for Clinical Trials in Chronic Lung Disease", Thorax, 1987, vol. 42, pp. 773-778.
Hillman, et al., "Introduction of the Medical Emergency Team (MET) System: a Cluster-Randomised Controlled Trial", Lancet, 2005, vol. 365, pp. 2091-2097.
Hurst, et al., "Susceptibility to Exacerbation in Chronic Obstructive Pulmonary Disease", The New England Journal of Medicine, 2010, vol. 363, No. 12, pp. 1128-1138.
Jolley, et al., "Neural Respiratory Drive in Healthy Subjects and in COPD", European Respiratory Journal, 2009, vol. 33, No. 2, pp. 289-297.
Kyroussis, et al., "Respiratory Muscle Activity in Patients with COPD Walking to Exhaustion With and Without Pressure Support", European Respiratory Journal, 2000, vol. 15, pp. 649-655.
Legrand, et al., "Mediolateral Gradient of Mechanical Advantage in the Canine Parasternal Intercostals", J. Appl. Physiol., 1996, vol. 80, No. 6, pp. 2097-2101.
Leidy, et al., "Standardizing Measurement of Chronic Obstructive Pulmonary Disease Exacerbations", American Journal of Respiratory and Critical Care Medicine, 2011, vol. 183, pp. 323-329.
Luo, et al., "Diaphragm Electromyography Using an Oesophageal Catheter: Current Concepts", Clinical Science, 2008, vol. 115, pp. 233-244.
Luo, et al., "Reproducibility of Twitch and Sniff Transdiaphragmatic Pressures", 2002, Respiratory Physiology & Neurobiology, vol. 132, pp. 301-306.
Mahler, et al., "Comparison of Clinical Dyspnea Ratings and Psychophysical Measurements of Respiratory Sensation in Obstructive Airway Disease", Am Rev Respir Dis, 1987, vol. 135, pp. 1229-1233.
Mahler, D., "The Measurement of Dyspnea During Exercise in Patients with Lung Disease", Chest, 1992, vol. 101, pp. 242S-247S.
Man, et al., "Effect of Salmeterol on Respiratory Muscle Activity During Exercise in Poorly Reversible COPD", Thorax, 2004, vol. 59, pp. 471-476.
Marin, et al., "Ventilatory Drive at Rest and Perception of Exertional Dyspnea in Severe COPD", Chest, 1999, vol. 115, pp. 1293-1300.
Martinez, et al., "Respiratory Response to Arm Elevation in Patients with Chronic Airflow Obstruction", Am Rev Respir Dis, 1991, vol. 143, pp. 476-480.
Murphy, et al., "Neural Respiratory Drive as a Physiological Biomarker to Monitor Change During Acute Exacerbations of COPD", Thorax, 2011, 7 pages.
Reilly, et al., "Neural Respiratory Drive, Pulmonary Mechanics and Breathlessness in Patients with Cystic Fibrosis", Thorax, 2011, vol. 66, pp. 240-246.
Roberts, et al., "Acidosis, Non-Invasive Ventilation and Mortality in Hospitalised COPD Exacerbations", Thorax, 2011, vol. 66, pp. 43-48.
Sharp, et al., "Thoracoabdominal Motion in Chronic Obstructive Pulmonary Disease", American Review of Respiratory Disease, 1977, vol. 115, pp. 47-56.
Steier, et al., "Neural Respiratory Drive in Obesity", Thorax, 2009, vol. 64, pp. 719-725.
Steier, et al., "Nocturnal Asthma Monitoring by Chest Wall Electromyography", Thorax, 2011, vol. 66, pp. 609-614.
Subbe, et al., "Validation of a Modified Early Warning Score in Medical Admissions", QJ Med, 2001, vol. 94, pp. 521-526.
Trappenburg, et al., "The Impact of Using Different Symptom-Based Exacerbation Algorithms in Patients with COPD", European Respiratory Journal, 2011, vol. 37, No. 5, pp. 1260-1268.

(56) References Cited

OTHER PUBLICATIONS

Ward, et al., "Respiratory Sensation and Pattern of Respiratory Muscle Activation During Diaphragm Fatigue", the American Physiological Society, 1998, pp. 2181-2189.
Quanjer, et al., "Lung Volumes and Forced Ventilatory Flows", European Respiratory Journal, 1993, vol. 6, Suppl. 16, pp. 5-40.

* cited by examiner

Fig. 1. Electrode placement for parasternal EMG

Fig. 2. Example of parasternal EMG trace (a) Record details
 · Signal quality assurance
 · electronic patient record
(b) Electromyogram raw signal with trend monitor of neural respiratory drive
(c) Neutral respiratory drive parameters
(d) Quality assurance for Sniff electromyogram signal

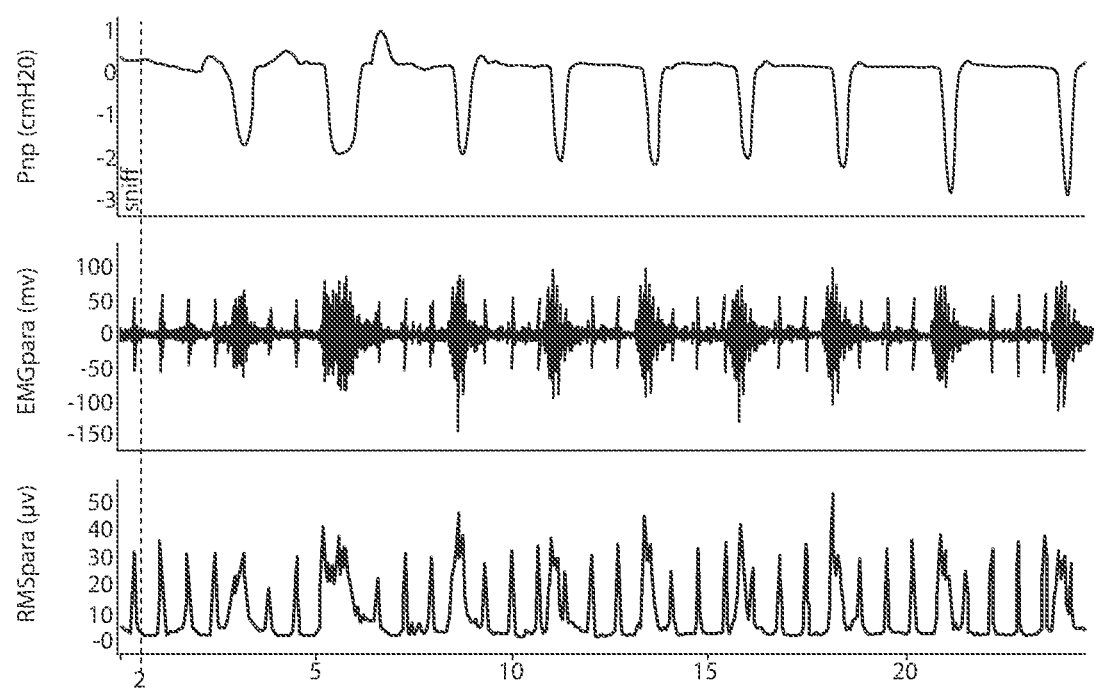

PATIENT MONITORING METHOD AND MONITORING DEVICE

CROSS-REFERENCE

This application claims the benefit of U.S. Provisional Patent Application No. 61/541,708, filed Sep. 30, 2011, and GB 1116860.6, filed Sep. 30, 2011, which applications are incorporated herein by reference in their entirety.

BACKGROUND

Various abbreviations are used throughout this application and for ease of reference those most frequently used are set out below:
EMG—electromyogram
ECG—electrocardiogram
COPD—chronic obstructive pulmonary disease
AECOPD—acute exacerbation of COPD
HR—Heart Rate
NRD—neural respiratory drive
NRDI—neural respiratory drive index
NRDTP—neural respiratory drive time product
NRDTI—neural respiratory drive time index
RR—respiratory rate
RMS—root mean square The use of physiological biomarkers to monitor and track clinical change in patients in both acute care organisations and in the community is an area of increasing interest to health care providers. Early detection of clinical deterioration and assessing the response to treatment correspond to improved clinical outcomes in patients. Despite the rationale for this approach, there is little published evidence to support the use of the current basic physiological monitoring systems available for detection of deterioration in patients as being sufficiently sensitive or having sufficient specificity for early detection (Hillman et al. (2005) *Lancet* 365, 2091-7).

Whilst heart rate (HR) and respiratory rate (RR) are commonly used clinical physiological variables in acute care, measurements of neural respiratory drive (NRD) and neural respiratory drive index (NRDI) are advanced physiological biomarkers that have been shown to have greater sensitivity and specificity in assessing the intensity, timing and duration of respiratory effort, which is defined by the balance between respiratory muscle load and capacity (Duiverman et al. (2004) *J. Appl. Physiol.* 96, 1723-9; Jolley et al. (2009) *Eur. Respir. J.* 33, 289-97; Steier et al. (2009) *Thorax* 64; 719-25).

Whilst this technique is an established research technique (Jolley et al. (2009); Steier et al. (2011) *Thorax* 66, 609-614; Murphy et al. (2011) *Thorax* 66, 602-8, incorporated herein by reference in its entirety), the limitations set out above have prevented it from becoming useful as a clinical tool. Indeed, the time involved in undertaking the analysis has limited its applicability to research situations. Whilst generic devices exist to perform the first steps of the process there is no known system available in clinical use to display NRD and NRDI as a physiological biomarker. One system utilises surface electrodes to measure EMG activity (Duiverman et al. (2004)), however, the commercial device has not been robust or reliable enough to move from the research to the clinical arena. Furthermore, the processing of the signal displays a log ratio of the EMG activity, which has no clinical advantage. In addition, this method has not focussed on an approach of normalisation of the $EMG_{para}$ signal to the maximal $EMG_{para}$ signal manoeuvre. These factors have prevented it from becoming a useful clinical tool.

SUMMARY

The present disclosure relates to a patient monitoring method and device. In particular, it relates to a method of, and device for, monitoring a patient with severe respiratory disease, and predicting the likelihood of both clinical deterioration and hospital re-admission.

According to an aspect of the present disclosure, there is provided a method of monitoring a patient, including measuring neural respiratory drive, repeating the measurement continuously and/or at regular time intervals, and comparing to the initial values measured in order to predict treatment failure and/or clinical deterioration and/or re-admission.

The neural respiratory drive may be measured by obtaining a measure of the second intercostal space parasternal electromyogram.

The method may include:
1) obtaining a value for a normalised neural respiratory drive (which may be calculated as $EMG_{para}/EMG_{paramax}$ and termed $EMG_{para\ \%\ max}$);
2) obtaining the respiratory rate of the patient, expressed as breaths per minute (RR/min);
3) obtaining a value for the neural respiratory drive index by multiplying the value of the neural respiratory drive obtained in Step 1 by the respiratory rate ($EMG_{para\ \%\ max} \cdot RR$);
4) repeating Steps 1 to 3 continuously and/or after a first given period of time and comparing the two neural respiratory drive index values obtained.

In an example, Steps 1 to 3 may be carried out upon admission into hospital and repeated just prior to discharge from hospital.

The method may further include obtaining a value for the neural respiratory drive time index by multiplying the value of the neural respiratory drive time product by the respiratory rate.

In an embodiment, the method includes:
1) obtaining a value for a normalised neural respiratory drive by:
a) carrying out parasternal electromyography to obtain a raw signal during normal breathing;
   identifying and obtaining the root mean square of the raw signal to obtain a rectified trace;
   identifying and obtaining the peak magnitude of the rectified trace for each inspiration;
   calculating the mean of the peak magnitudes identified ($EMG_{parapeak}$);
b) carrying out parasternal electromyography to obtain a raw signal during at least two (or at least three) sniff maximal manoeuvres;
   obtaining the root mean square of the raw signal to obtain a rectified trace;
   identifying and selecting the peak magnitude of the rectified trace ($EMG_{paramaxpeak}$);
c) expressing the mean of the peak calculated in Step 1a as a percentage of the peak magnitude selected in Step 1b ($EMG_{para\ \%\ maxpeak}$)
2) obtaining the respiratory rate of the patient, expressed as breaths per minute;
3) obtaining a value for the neural respiratory drive index by multiplying the value of the $EMG_{para\ \%\ maxpeak}$ (NRD) obtained in Step 1c by the respiratory rate;

4) repeating Steps 1 to 3 continuously and/or after a first given period of time and comparing the two neural respiratory drive index values obtained.

In one embodiment, the first period of time is selected from the range of 8 to 24 hours. For example, an initial measurement may be taken upon hospital admission, with a second measurement being taken 8 to 24 hours after admission. Optionally, the measurement and comparison is performed continuously or repeatedly at an approximate frequency of the first period of time.

Additionally or alternatively, the method may include:
obtaining a value for the neural respiratory drive time product by carrying out parasternal electromyography to obtain a raw signal during normal breathing;
obtaining the root mean square of the raw signal to obtain a rectified trace;
measuring the area under the rectified trace;
obtaining a value for the neural respiratory drive time product index by multiplying the neural respiratory drive time product by the respiratory rate; and
comparing the two neural respiratory drive time index values obtained.

The method may include identifying and obtaining the area under the curve of the rectified root mean square of the raw signal; calculating the mean of the area under the curves identified ($EMG_{paraAUC}$); identifying and selecting the area under the curve of the rectified trace ($EMG_{paramaxAUC}$); expressing the mean area under the curve as a percentage of the maximum area under the curve ($EMG_{para\ \%\ maxAUC}$) and obtaining neural respiratory drive time index by multiplying the value of the $EMG_{para\ \%\ maxAUC}$ (NRDTP) by the respiratory rate.

In embodiments, the patient has respiratory disease, (for example, cardiorespiratory disease). The respiratory disease may be (1) an acute exacerbation of chronic obstructive pulmonary disease; (2) an acute exacerbation of chronic respiratory disease; (3) acute respiratory failure; (4) chronic respiratory disease; (5) chronic respiratory failure; (6) acute exacerbation of chronic heart failure (7) acute heart failure and (8) chronic heart failure, for example.

The method may be used to predict clinical deterioration and/or the likelihood of hospital readmission within 28 days of discharge.

In an embodiment, the peak magnitude is obtained for each inspiration over a time period of approximately 30 seconds to 3 minutes.

In some cases, the neural drive index values and/or the neural respiratory drive time product index values are obtained upon admission to hospital, intermittently or continuously throughout admission until the day of discharge from hospital. The NRD, NRDI, NRDTP and NRDTI may alternatively be obtained in the community or home setting either intermittently at various time points (for example, each day after hospital discharge) or continuously.

In an exemplary embodiment, the method includes obtaining an electrocardiography signal, and removing artifacts from the electrocardiography signal from the raw parasternal electromyography trace.

As an example, the monitoring can be carried out in real time.

According to another aspect of the present disclosure, there is provided a monitoring device including a signal input, a processing unit, and an output unit, the monitoring device being arranged to:
(1) receive a first raw parasternal electromyography signal at the signal input;
(2) determine the root mean square of the raw parasternal signal to obtain a rectified trace;
(3) identify the peak magnitude of the rectified parasternal trace for each inspiration over a second given period of time;
(4) calculate the mean of the peak magnitudes identified;
(5) receive further and determine raw parasternal electromyography signals during at least two (or at least three) sniff manoeuvres;
(6) determine the root mean square of the raw signal to obtain a further rectified trace;
(7) determine the peak magnitude of the further rectified trace;
(8) express the mean of the first peak magnitude as a percentage of the peak magnitude of the further rectified trace obtained during the sniff manouevre;
(9) receive data on the respiratory rate of the patient, expressed as breaths per minute;
(10) determine a value for the neural respiratory drive index by multiplying the value of the neural respiratory drive by the respiratory rate;
(11) store the measured/determined values of the neural respiratory (for example, NRD and NRDI, and optionally NRDTP and NRDTI) in the data repository.

In some embodiments, the monitoring device is arranged to determine a subsequent neural respiratory drive index and compare with the stored value.

In some embodiments, the monitoring device is also operable to identify the area under the curve of the rectified root mean square of the raw parasternal signal for each inspiration over a second given period of time; to calculate the mean of the area under the curves identified; and to determine the values for NRDTP and NRDTI from the area under the curve of the rectified trace.

In some cases, the monitoring device is operable to display the measured/determined neural respiratory drive values (for example, NRD and NRDI, and optionally NRDTP and NRDTI) in real time.

Embodiments of the present disclosure provide for substantially real time processing of biological signals received from surface electrodes and convert them into a clinically useful physiological biomarker. The signals from these electrodes are processed in one embodiment to obtain and display heart rate (HR), respiratory rate (RR), neural respiratory drive (NRD), neural respiratory drive index (NRDI), and optionally neural respiratory drive time product (NRDTP) and neural respiratory drive time index (NRDTI). Whilst HR and RR are commonly used clinical physiological variables in acute care, the NRD and NRDI have been shown to be more sensitive markers of neural respiratory drive and respiratory effort and have previously been shown to correspond to the balance between the respiratory muscle load and the respiratory muscle capacity. Additionally or alternatively NRDTP and NRDTI may be used.

NRD can be determined from the electromyogram of the 2nd intercostal parasternal muscles ($EMG_{para}$). These are acquired using electrodes and amplifiers and the signals are processed using analogue to digital conversion followed by digital filtering and arithmetic conversion of the signal.

In one embodiment, signals are recorded during resting breathing to provide an indication of the patient's current respiratory effort determined by objectively measuring the $EMG_{para}$ activity. At the end of recording, the patient is asked to perform repeated maximum sniff manoeuvres in order to allow the signal to be normalised for an individual patient maximum effort ($EMG_{para\ \%\ max}$).

In one embodiment, the process of acquiring these biological signals and producing clinical useful data is divided into a four step process, with the final step of integrating and processing the parasternal electromyogram. The steps involved are detailed below:

1. Patients at potential risk of deterioration are identified (for example, upon acute admission to hospital) by clinical staff and have surface electrodes placed over the parasternal muscles of the second intercostal space along with a reference electrode over the electrically neutral clavicle.
2. Electrical signals from the two recording electrodes are amplified. The signal is amplified to a factor of 1000 and analogue filtered at 10 Hz and 2000 Hz to remove contributions from other muscle activity and maximise signal from the parasternal muscles.
3. The amplified signal is passed to an analogue to digital converter to allow for further computer processing.
4. The final step of the process is to integrate the signals to produce the essential biological variables for clinical interpretation. The initial signal is assessed for signal quality and advises if repositioning of the electrodes is required. If signal quality is adequate the patient performs a series of maximum sniff manoeuvres in order to normalise the signal for individual variations in subcutaneous fat distribution that can alter signal strength. Once the system has detected and analysed the maximum manoeuvres the patient undergoes a period of testing that comprises of relaxed breathing at which time continuous measures of HR, RR and NRD, NRDI, and optionally NRDTP and NRDTI are displayed. The $EMG_{para}$ signal is processed to remove ECG artefact by a simple 20 Hz digital filter. As the signal comprises of positive and negative deflections further processing occurs to produce a representative value by converting the $EMG_{para}$ to a root mean squared (RMS) with a moving window of 40 ms. As well as displaying the previously used marker of NRD ($EMG_{para}$), NRDI is displayed that incorporates respiratory rate to provide a measure of neurological drive to breathe over a minute rather than the per breath measure provided by $EMG_{para}$.

In selected embodiments, some or all of the following features may apply or be included:
  Signal quality assessment
  ECG (QRS) detection and HR calculation
  ECG artefact removal from $EMG_{para}$ signal
  Calculation of the RMS
  $EMG_{para}$ analysis including peak-peak analysis to calculate respiratory rate, peak value to calculate $EMG_{para\ \%\ maxpeak}$ and multiplication by respiratory rate to calculate NRDI
  $EMG_{para}$ analysis to calculate area under the curve of the signal to calculate $EMG_{para\ \%\ maxAUC}$ by normalizing for the $EMG_{paramaxAUC}$ and multiplying by respiratory rate to calculate NRDTI Other potential uses in both hospital and home setting include:
Home:
  Objective measure of breathlessness in patients with chronic respiratory disease, for example COPD
  Identification of patients undergoing clinical deterioration, for example. an exacerbation of COPD
  Facilitation of the out of hospital set up of patients with chronic respiratory failure (for example, COPD, neuromuscular disease and obesity hypoventilation syndrome) requiring domiciliary non-invasive ventilation allowing improved set up without hospital admission, of particular benefit in conditions associated with a poor prognosis. The proposed approach is to optimise patient-ventilator interaction using NRD, NRDI, and optionally NRDTP and NRDTI as an objective physiological biomarker.

Hospital:
  Monitoring respiratory deterioration in acute critical illness
  Facilitate setup of domiciliary non-invasive ventilation in patients with chronic respiratory failure
  Facilitate setup for acute non-invasive ventilation in patients with acute and acute on chronic respiratory failure
  Stratification of patients that are high risk of re-admission Potential benefits of selected embodiments include:
  Real time display of important clinical parameters
  Data log for trend display of changes in parameters
  Single tool for six clinical parameters (HR, RR, NRD, NRDI, NRDTP and NRDTI)
  Signal analysis and processing to allow removal of ECG artefact and computing neural respiratory drive
  Use of neural respiratory drive as a clinical respiratory biomarker

BRIEF DESCRIPTION OF THE DRAWINGS

Exemplary embodiments of the present disclosure are described below with reference to the accompanying drawings, in which:

FIG. 11 shows daily changes in (A) $EMG_{para\ \%\ max}$ and (B) NRDI during the course of admission between patients designated as 'improvers' or 'deteriorators' during the first 24 hours of study participation (plotted as mean±standard error of the mean);

DETAILED DESCRIPTION

Figure 1:
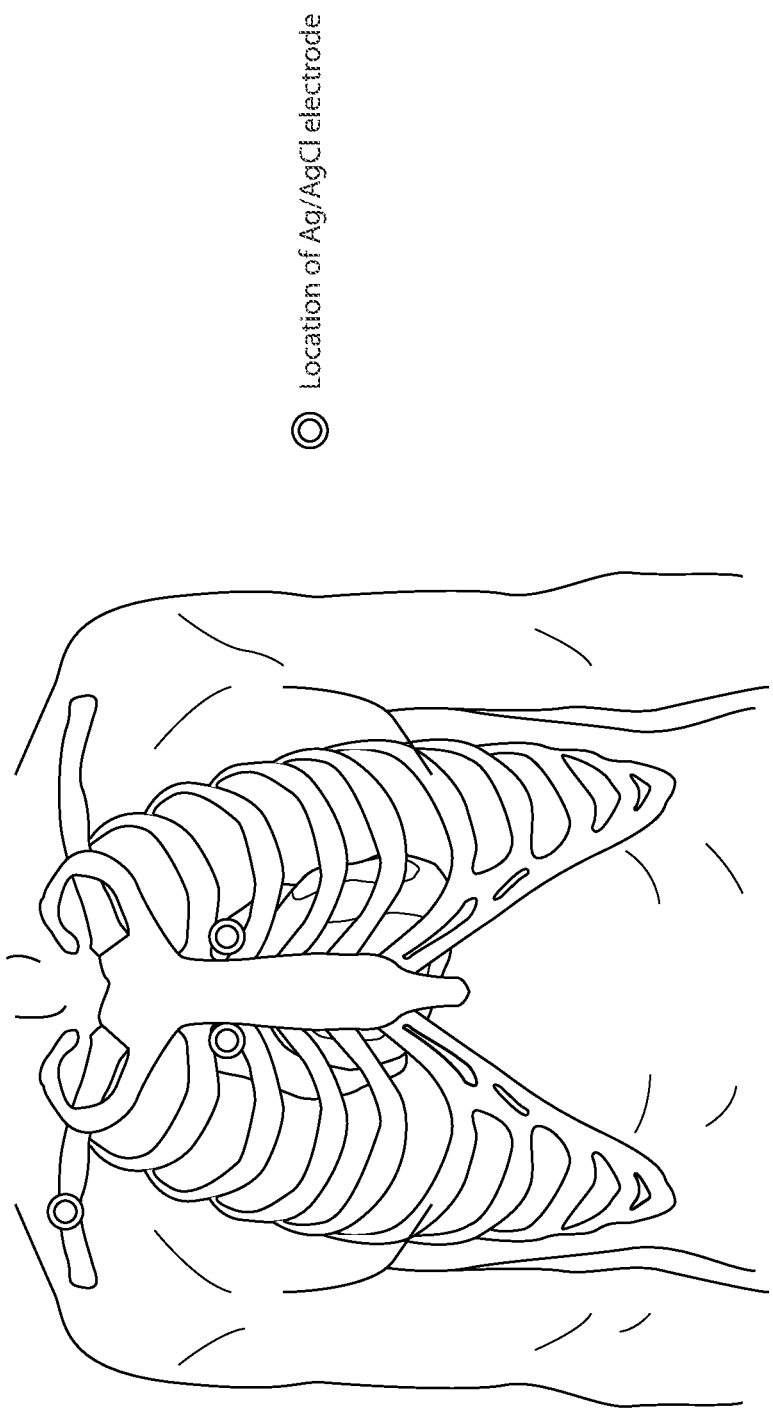
FIG. 1 illustrates exemplary electrode placement locations.

NRD is calculated from the electromyogram of the $2^{nd}$ intercostal parasternal muscles ($EMG_{para}$). These signals can be acquired using conventional electrodes and amplifiers. The signals may be processed using basic analogue to digital conversion followed by digital filtering and arithmetic conversion of the signal. The subsequent digitised and converted signal is hand analysed discounting sections of the trace that have interference from the electrical signals of the heart muscle, or electrocardiogram (ECG).

This technique requires the signals to be recorded during resting breathing to provide an indication of the patient's current respiratory effort based on their $EMG_{para}$ activity. At the end of recording, the patient is asked to perform repeated maximum sniff manoeuvres in order to allow the signal to be normalised for an individual patient maximum effort ($EMG_{para\ \%\ max}$). The data are then manually analysed off-line at a later time with each breath being manually marked, measured and breaths contaminated by ECG artefact being removed.

The device 10 includes a signal input 20, a processing unit 30, a data repository 40 and an output unit 50.

The device 10 receives a signal at the signal input 20 that has been measured from the parasternal electromyogram (EMG).

Figure 4:
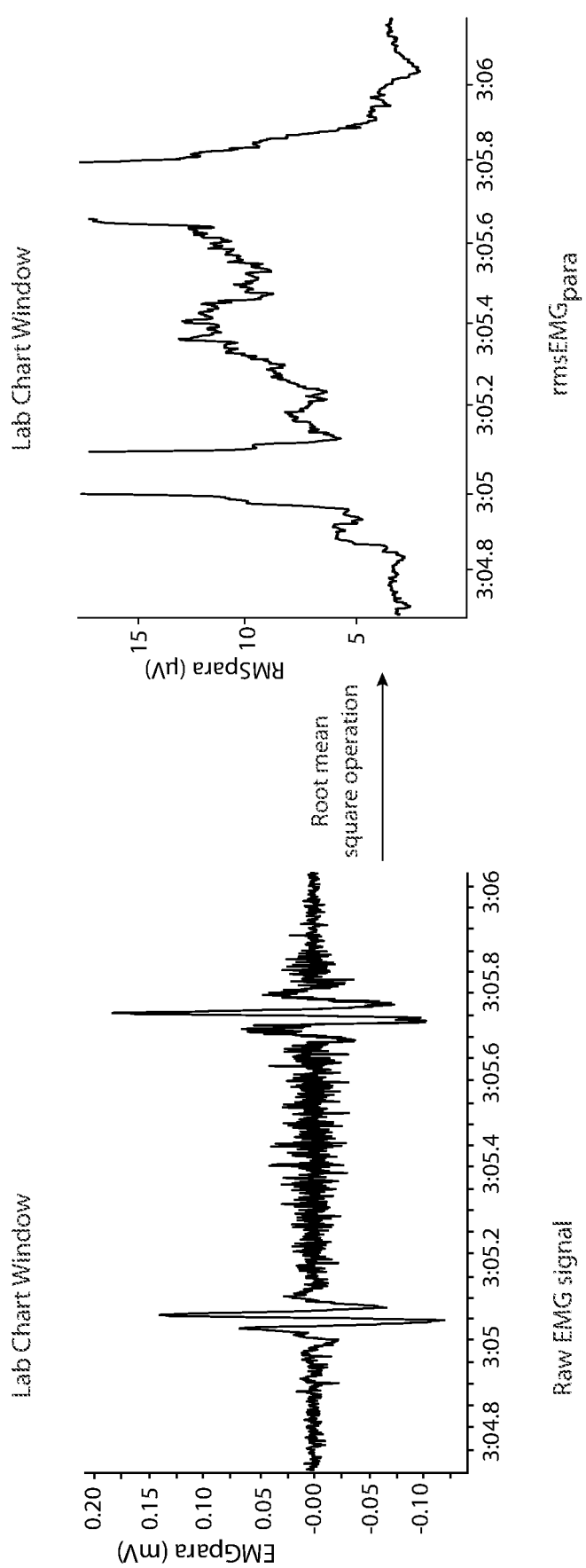
FIGS. 4 to 7 are illustrations of signals during processing of an embodiment of the present disclosure.

The signal is passed to the processing unit 30 where the raw, biphasic parasternal EMG signal is rectified using a root mean square operation as shown in FIG. 4. Preferably, a window is used to segment the signal and simplify RMS calculation.

$$rms(n) = \sqrt{\frac{\sum_{n-M}^{n+M} resp^2(i)}{2M}}$$

with M=25 ms×Fs=50 samples.

Figure 5:
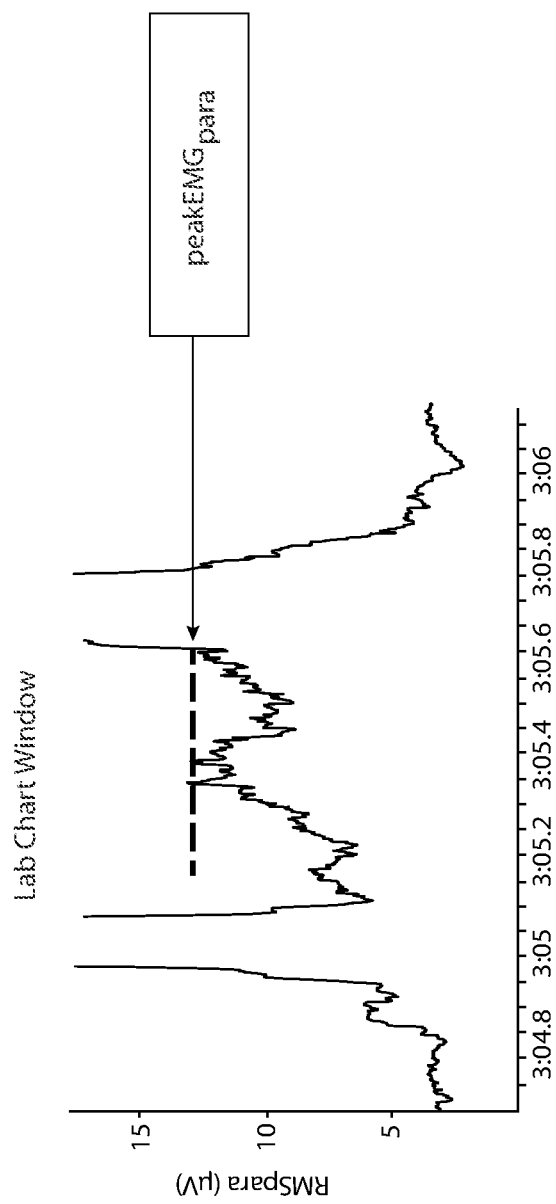

The peak magnitude ($EMG_{parapeak}$) of the rectified rmsEMG$_{para}$ trace is then identified by the processing unit 30 for each inspiration over 30 seconds to 3 minutes as shown in FIG. 5.

The mean of the $EMG_{parapeak}$ values is then calculated for all inspirations over a 30-second to 3 minute time period. This is termed mean ($EMG_{parapeak}$).

Figure 6:
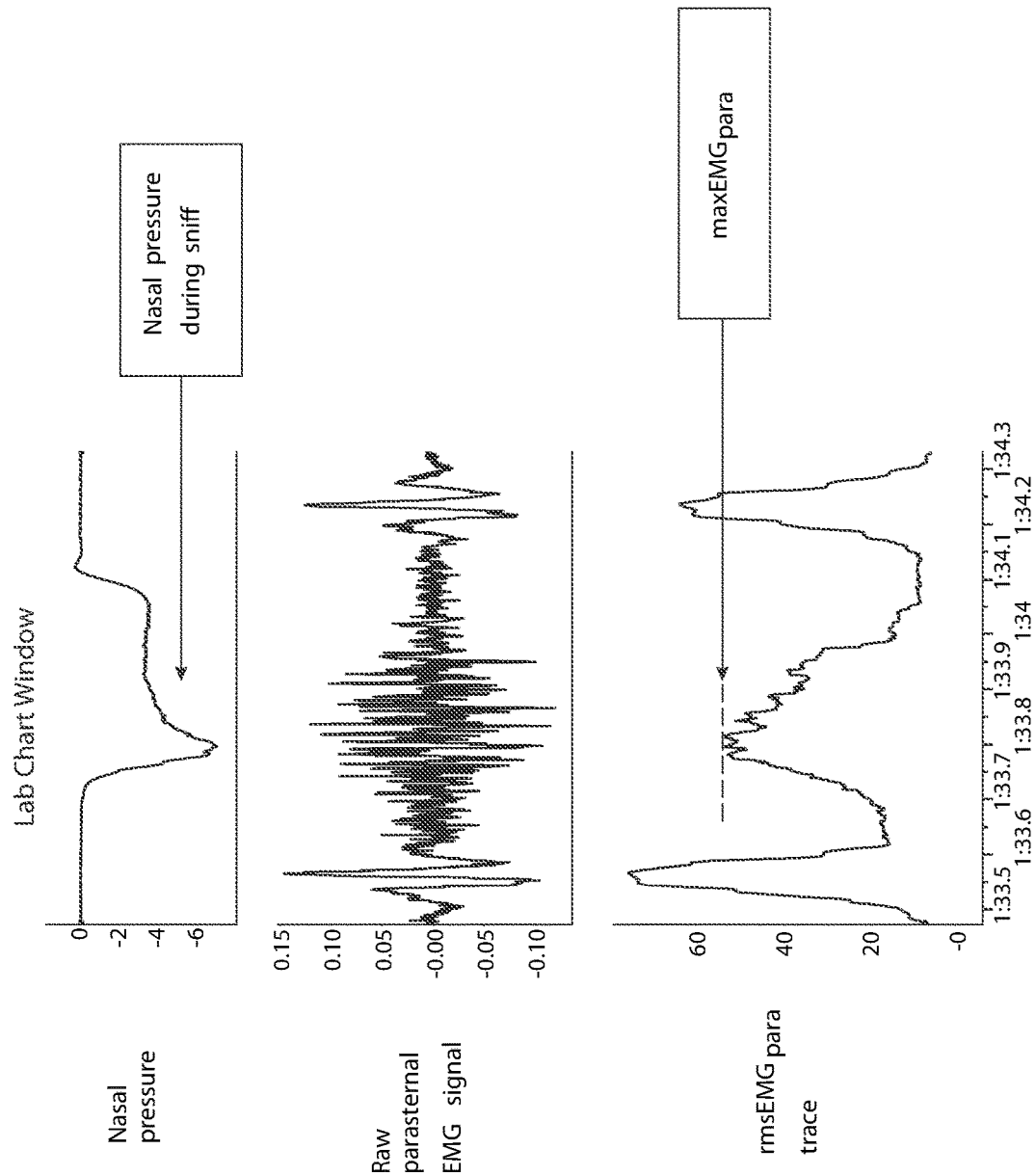

The magnitude of the rmsEMG$_{para}$ trace during a maximal inspiratory manoeuvre is recorded as shown in FIG. 6.

In practice, the patient performs several sniff manoeuvres. The manoeuvre that results in the greatest magnitude of rmsEMG$_{para}$ is selected. This value is termed $EMG_{paramax}$ The neural respiratory drive is represented by the quantity $EMG_{para\ \%\ max}$. This is derived by expressing the mean ($EMG_{parapeak}$) as a percentage of the $EMG_{paramax}$:

$$EMG_{para\ \%\ max} = [mean(mean(EMG_{parapeak})/EMG_{paramax}] \times 100\% \quad (1)$$

The Neural Respiratory Drive Index (NRDI) is then calculated by the processing unit 30.

NRDI is the product of $EMG_{para\ \%\ max}$ and the respiratory rate (RR, breaths per minute)

$$NRDI = EMG_{para\ \%\ max} \times RR \quad (2)$$

Figure 7:
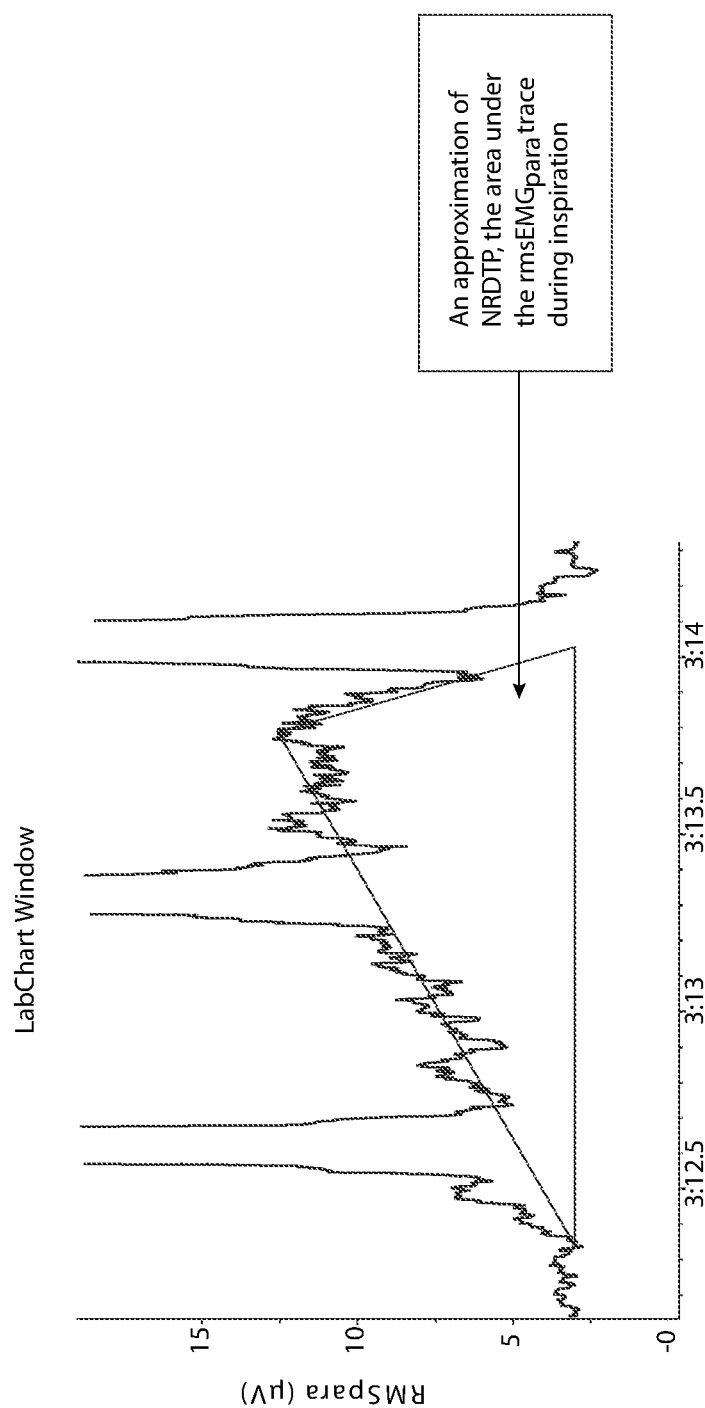

The area under the curve of the rmsEMG$_{para}$ trace, termed neural respiratory drive time product; NRDTP, is then calculated as shown in FIG. 7. This approximation is used to enable substantially real time processing, although it will be appreciated that more accurate measurements could be made. NRDTP indicates the total electrical activity of the muscle during inspiration, a non-invasive surrogate for the work of breathing.

The neural respiratory drive time index (NRDTI) is the product of NRDTP and respiratory rate normalised for the $EMG_{paramaxAUC}$:

$$NRDTI = NRDTP \times RR \quad (3)$$

NRDTI more accurately reflects the total neural respiratory drive compared to NRDI, as the latter takes into account only the peak value of the parasternal EMG signal during each inspiration. By contrast, the area under the rmsEMG$_{para}$ curve represents the electrical activity of the parasternal muscles during the whole of inspiration.

The device 10 automatically calculates the NRDTI and stores it in the data repository 40. Subsequent measurements and calculations are stored in the data repository and compared to earlier values of NRDTI. A reduction in value is indicative of reduced likelihood of re-admission. A consistent value or an increase is indicative of higher likelihood of re-admission.

The presence of ECG (cardiac) signal artefact in the parasternal EMG trace significantly affects accurate analysis of neural respiratory drive.

Figure 8:
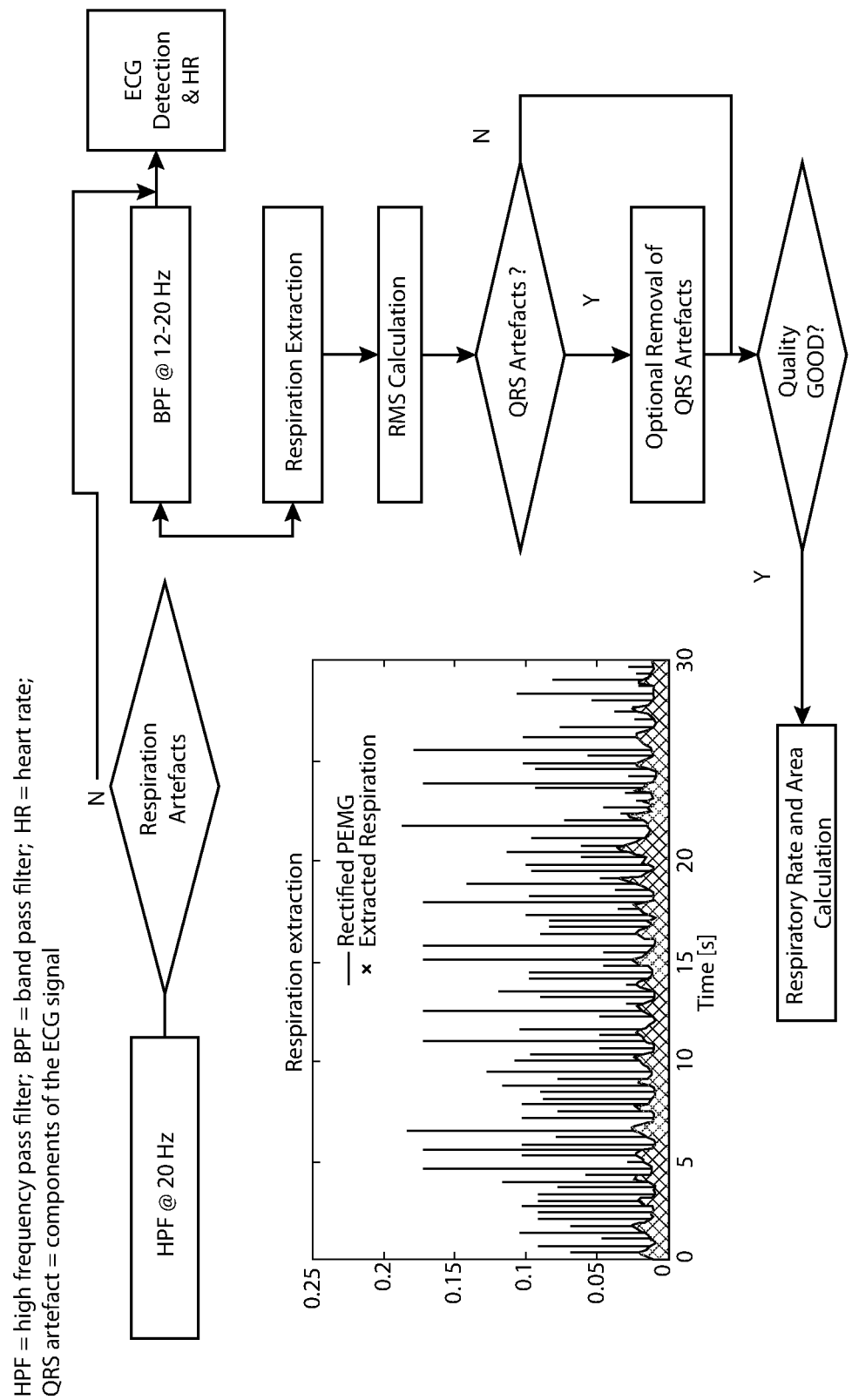
FIG. 8 is a flow diagram illustrating aspects of filtering and subsequent steps of a method according to an embodiment of the present disclosure.

In exemplary embodiments of the present disclosure, the processing unit 30 applies a filtering algorithm to remove the ECG artefact from the raw parasternal EMG trace. Aspects of the algorithm are shown in FIG. 8. A high pass filter is applied to the raw signal to remove baseline noise.

Additional band pass filtering (BPF) between 12-20 Hz is performed to condition the signal spectral content to remove respiration artefacts prior to ECG detection when high levels of neural respiratory drive are present. This additional filtering is based on the principle that the electromyogram is a broad-band signal, whilst the QRS complex of the ECG main spectral content is below 20 Hz and the empirical observation (from previous patient data) that patient with low NRD have $EMG_{para}$ signals with a spectral content above 0.4 Hz less than 60%.

ECG detection can be carried out by comparison of a non-linear derivation of the first derivative of the filtered $EMG_{para}$ signal with a threshold. The algorithm is an implementation of a QRS complex detection algorithm which is particularly suitable for signals (such as $EMG_{para}$) affected by motion artefacts. The specific threshold (Speak=0.0001) used by the algorithm was chosen empirically, as best performing (90% Sensitivity) in the range $10^{-5}$-$10^{-2}$ when testing the algorithm on 52 different blocks of data of 20-30 s length.

In some patients residual influence of QRS peaks would lead to outlier peaks in the rmsEMG$_{para}$, which can be removed by the activation of an optional routine.

The routine examines the distribution of the peaks in a window of 30 s of rmsEMG$_{para}$ signal, calculates their 99.3 percentile (P993, a value above 99.3% of all peaks) and compares it with the maximum in the distribution (rmsEMG$_{paramax}$). If P993/rmsEMG$_{paramax}$<0.7 then all the peaks above P993 are considered outliers and eliminated.

Knowledge of the location of the QRS peaks is used to eliminate the contribution of a patient's ECG to a $EMG_{para}$ signal. In particular, following the example of previous studies only a portion of signal between two R peaks is kept. The portion of rectified signal between 30%-75% of each R-R interval is considered as respiration only and is kept unmodified. For example, if one R peak is at 10 s and the following one is at 10.8 s (R-R interval=800 ms), then the portion of signal between 10.24 s (10 s+30% of 800 ms) and 10.6 s (10 s+75% of 800 ms) it is left unchanged. A larger interval than previous studies was used to avoid loss of data. The portions of signals corresponding to QRS complexes are replaced by linear interpolations connecting adjacent unmodified data segments. In the designing phase zero padding, zero order interpolation and the use of the root means square of two adjacent segments were also attempted, but discarded. This is because these options were affecting the signal morphology to a point where each respiration peak would be split in two and the software would return a doubled respiration rate.

It will be appreciated that the use of a real time measure of NRD could be used not only on other patients with acute respiratory illness but also in the long term management of chronic disease. The technique is simple and quick to perform and is totally painless for the patient and could be applied in clinic patients for the monitoring of chronic respiratory disorders such as COPD, obesity related respiratory failure (for example, obesity hypoventilation syndrome and hypercapnic obstructive sleep apnoea), asthma, bronchiecteasis, neuromuscular disease and interstitial lung disease in order to more sensitively track clinical change. The technique also offers the opportunity to closely monitor and optimise patient-ventilator interaction in patients receiving both acute and domiciliary non-invasive ventilation (NIV). NIV confers significant clinical outcome benefits to patients with acute and chronic respiratory failure but its use can be limited by poor patient tolerance as a consequence of poor adherence to the ventilator prescription resulting from poor patient-ventilator interaction. The ability to match patient and ventilator effort would offer the opportunity of improving patient comfort and thus improve the adherence to therapy. The potential uses in the home setting are:

Objective measure of breathlessness in patients with chronic respiratory disease for example, COPD Identification of patients undergoing clinical deterioration for example, an exacerbation of COPD Facilitation of the out of hospital set up of patients requiring domiciliary NIV allowing improved set up without hospital admission, of particular benefit in conditions associated with a poor prognosis.

In one embodiment, a monitoring device may be connected to a patient in the home and measurement communicated (for example via a mobile data connection, WIFI etc.) back to a server at the hospital for monitoring, analysis which would be supported by a clinical team utilising a clinical decisions algorithm leading to clinical intervention. For example, the patient can be monitored remotely and if the patient's clinical condition were to deteriorate this would be identified by a change in RR, HR, NRD, NRDI, and/or NRDTP, NRDTI as described above with an alert communicated to the clinical team. The clinical team would alert the patient and/or carer either through the device or directly to advise the patient and/or carer to seek medical attention. Alternatively, or in addition, an automated call could be made to a designated phone number to provide an alert. Appropriate medical intervention can then be carried out.

The potential uses are in the hospital setting are:
Monitoring respiratory deterioration in acute critical illness
Facilitate setup of NIV for domiciliary NIV
Facilitate setup for acute NIV
Stratification of patients that are high risk of re-admission
Where a patient is identified as being at high risk of hospital re-admission, changes can be made to their medical care so that it can be optimised; hospital discharge could be delayed; and/or after outreach support may be intensified (for example a carer may visit twice daily instead of only once).

Figures 9A, 9B, 9C, 9D:
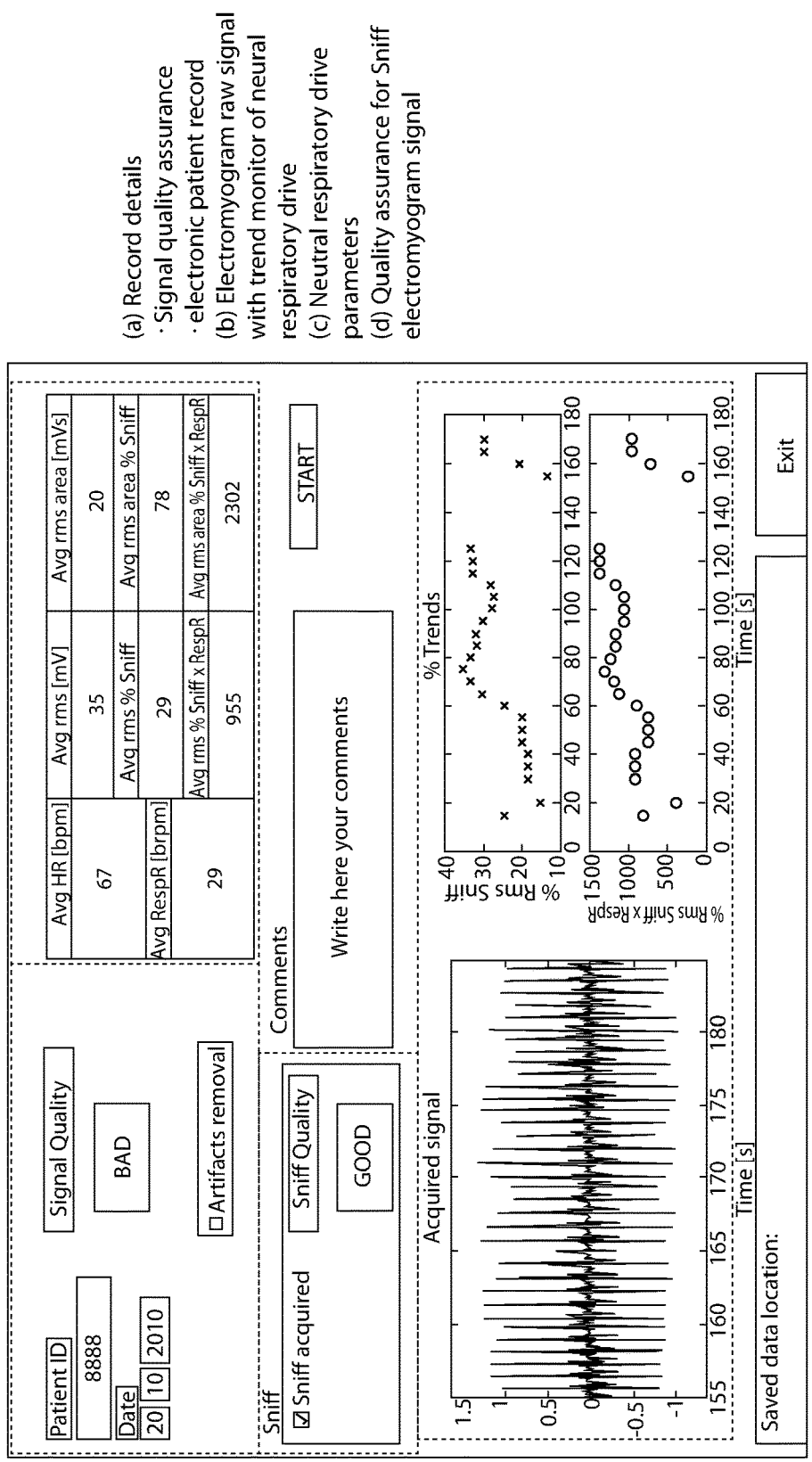
FIGS. 9A-9D are screen shots of an output produced in an embodiment of the present disclosure.

The monitor display produced, as shown in FIG. 9, allows the monitoring and recording of 'resting' breathing and the 'Sniff manoeuvre'.

Figure 2:
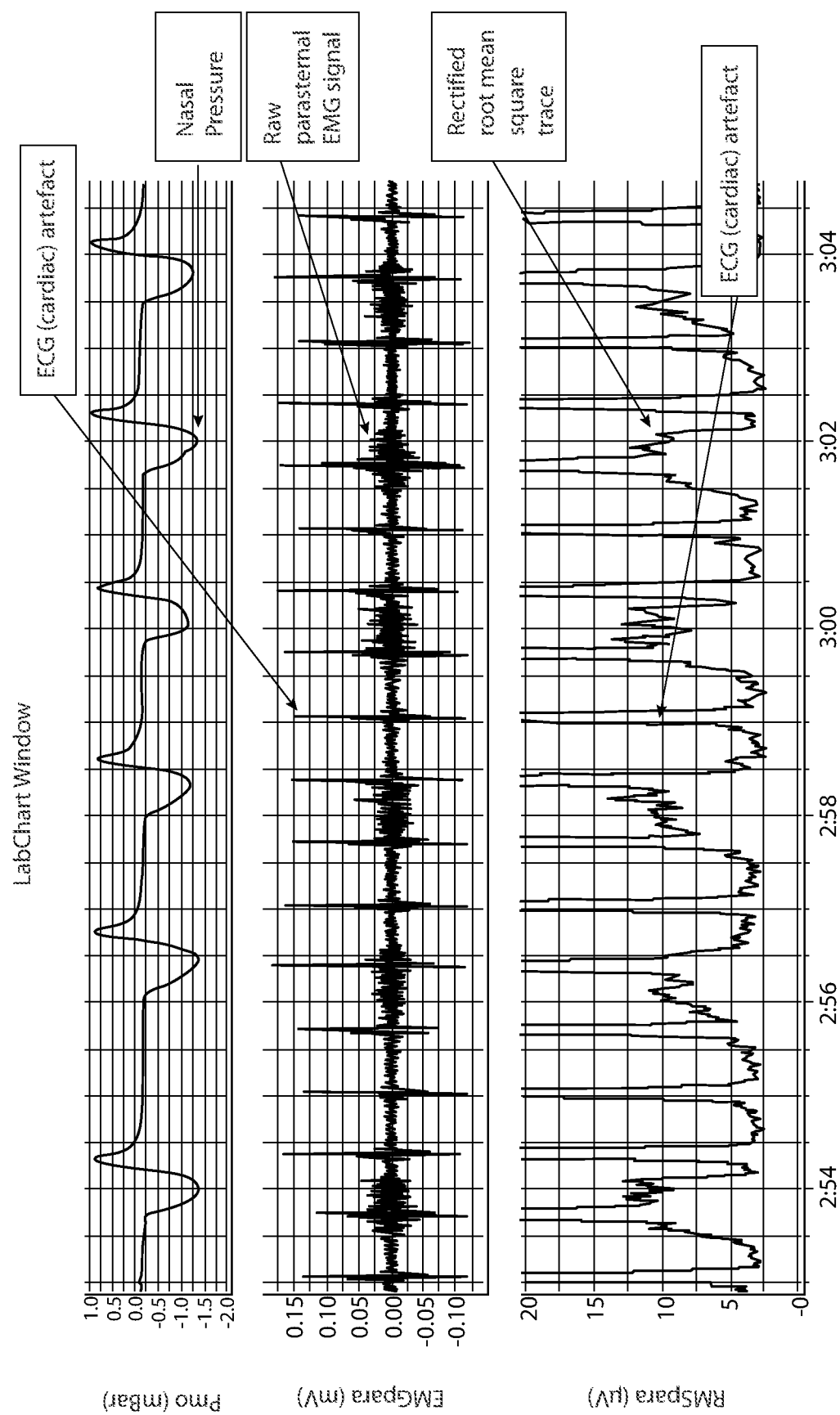
FIG. 2 illustrates a sample signal in both raw and partially processed states.
Figure 3:
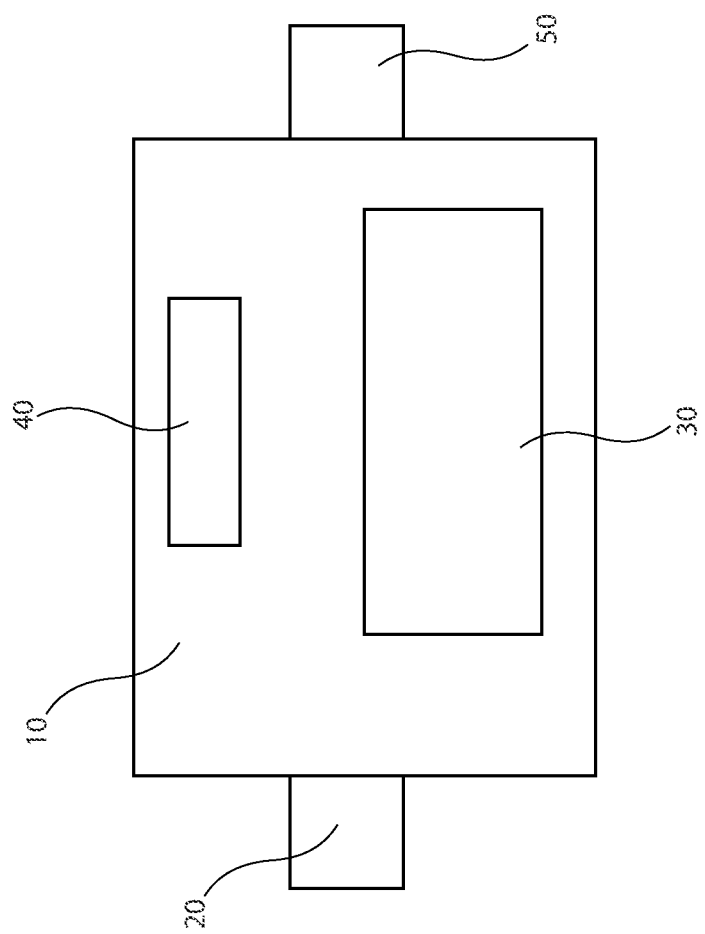
FIG. 3 is a schematic diagram of a monitoring device according to an embodiment of the present disclosure.

The patient is identified by a unique 'Patient ID' integer number (FIG. 2-(a)), that the operator can choose; the monitoring 'Date' is automatically set-up by the program.

The monitoring device is set to collect 5 s of data a time at a frequency of 2 kHz such as by a National Instruments USB DAQ device (NI BNC 6221) and return an immediate feedback on 'Signal Quality', based on a comparison of detectable respiratory activity and background noise level.

Once at least 30 s of resting data have been acquired the monitor will display the following signal features:

Avg HR [beats per minute]: average heart rate in beats per minutes in the last 30 s to 3 minute sampling period Avg RR [breaths per minute]: average respiration rate in breath per minute in the last 30 s to 3 minute sampling period Avg rms [mV]: average peak root mean square in mVolts in the last 30 s to 3 minute sampling period In case of data of poor quality with low NRD, only the HR might be extractable, in such cases a 'NaN' (Not a Number) will be returned for the other parameters. Whenever possible, it is advised not to proceed with data of 'BAD' quality and to check the electrode contact to assess if it possible to gain data of 'GOOD' quality.

The quality of a resting segment is considered 'GOOD' if the $EMG_{para}$ signal is easily distinguishable from noise. The algorithm calculates a threshold equal to 40% of a smoothed $EMG_{para}$ signal and determines if it can detect $EMG_{para}$ peaks above this threshold. If $EMG_{para}$ peaks are detectable, the signal is considered of 'GOOD' quality and an average RR is estimated from the intervals between the detected peaks. Otherwise the signal is considered of 'BAD' quality and the RR is set equal to 'Not a number' (NAN).

As signal quality is updated every 5 s, one can expect samples with no respiration activity, therefore flagged as 'BAD', during a continuous acquisition. Whenever the operator is flagged constantly 'BAD' quality the acquisition should be interrupted and electrode contact with the patients and the rest of the acquisition variables should be checked to improve signal quality.

Once the operator (for example, nurse, doctor, technician) is satisfied that the data are 'GOOD' quality, the patient will be asked to perform a 'sniff manoeuver', and 10 s to 20 s of 'sniff manoeuver' data should be collected pressing the 'START SNIFF' button in the 'Sniff' sub-panel (FIG. 2-(d); button not shown in figure).

The same features as above are returned in a 'sniff manoeuver' session if the sniff signal is of 'GOOD' quality, however, in case of the 'sniff manoeuver', peak values and area under curve rather than average peak values are considered.

Once 'GOOD' quality sniff data have been acquired, the operator can proceed with monitoring of resting traces and receive the additional feedback on NRD, NRDI, NRDTP and NRDTI for the last recorded 30 s:

FIG. 9 is a screen shot of a possible user interface produced in one embodiment of the present disclosure. The interface is organised into different blocks.

Block (a) reports the treatment details (Patient ID and Date), the signal quality, and a 'checkbox' that enables further removal of ECG artifacts from NRD signals.

Block (b) shows the last 30 s of signal acquired on the left, and the trends of the two important NRD features on the right: '% rms sniff' (30 s average $EMG_{peakpara}/EMG_{paramax}$=NRD) and % rms sniff×RR (30 s average $EMG_{peakpara}/EMG_{paramax}$×RR=NRDI) since monitoring started. These trends are only shown after a 'sniff' $EMG_{para}$ signal has been acquired.

Block (c) reports values averaged on 30 s of all the features extracted: Avg HR (average heart-rate), Avg rms (average peak rms), Avg rms area (average area under the rms curve), Avg RespR (average respiratory rate), Avg rms % sniff (average rms normalized to the 'sniff' peak rms value), Avg rms area % sniff (average area normalized to the 'sniff' peak rms value), Avg rms % sniff×RespR (Average rms % sniff multiplied by the respiratory rate), Avg rms area % sniff×RespR (% Average rms area % sniff multiplied by the respiratory rate). The last four parameters are available only if a sniff signal has been acquired.

Block (d) shows the information about the sniff signal acquired. Prior to 'sniff' acquisition it also contains a 'START Sniff' button that allows the acquisition of a 10 s 'sniff' trace. The interface also has a 'comment' box and one showing where the acquired data are saved. A 'START' button allows the beginning of a monitoring phase.

The applicant has shown that NRDI is a feasible clinical physiological biomarker in patients with an acute exacerbation of chronic obstructive pulmonary disease (COPD), which can provide useful information on treatment response and risk of hospital readmission (Murphy et al. (2011)). It has shown that the technique of measuring NRDI to monitor patients with COPD has potential across acute care services, critical care services and community services. In patients with COPD, the signals have been shown to be wholly reproducible and more sensitive and specific than standard clinical parameters at monitoring clinical change, and more importantly clinical deterioration. NRDI was also shown to be useful in risk stratifying readmission in COPD patients following discharge from hospital following an acute exacerbation.

The use of the above-described monitoring device and method has a number of advantages: (1) it is less time consuming; (2) data points are separated from the ECG signal and are therefore not lost; (3) signal analysis and clinical interpretation are performed in real time; and (4) the opportunity to modify the clinical management if the NRD signal does not change in response to treatment is provided.

At least a portion of the embodiments described herein may be performed by a process defined by code executing within a processor of a computer, state machine of suitably configured hardware based processor such as a field programmable gate array (FPGA). The code can comprise software instructions that are provided to a physical memory that is accessible to the processor of the computer. The code can be arranged as firmware or software, and can be organized as a set of modules such as discrete code modules, function calls, procedure calls or objects in an object-oriented programming environment. If implemented using modules, the embodiment can comprise a single module or a plurality of modules that operate in cooperation with one another.

It will also be appreciated that embodiments of the present disclosure are possible in which processing may be done locally (for example at a hospital bedside, in a patient's home using portable measuring equipment) or remotely (in which case the monitoring device may simply capture raw data and transmit back to a remote server such as via ftp, a secure Web interface or some other communication means and then processed at the server) In one embodiment, a centralized user interface, for example in the form of an on-screen dashboard, can provide filtered up-to-date results to medical staff for a number of patients, both local and/or remote so that semi-automated tracking of status can be done and fed to a remote station for review.

Optional embodiments of the disclosure can be understood as including the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although illustrated embodiments of the present invention have been described, it should be understood that various changes, substitutions, and alterations can be made by one of ordinary skill in the art without departing from the present invention which is defined by the recitations in the claims below and equivalents thereof.

EXAMPLES

Example 1—Validation of Reproducibility of $EMG_{para}$

Methods

Subjects $EMG_{para}$ measurements in healthy volunteers were taken one week apart. $EMG_{para}$ measurements from stable COPD patients were recorded at consecutively attended classes, 3 to 4 days apart.

$EMG_{para}$ Recording and Data Processing

The second intercostal space was identified using bony landmarks and skin was prepared with EMG contact gel (Nuprep, DO Weaver and Co, USA). Wet gel electrodes (Neuroline 720, Ambu, Denmark) were placed adjacent to the sternal edge in the second intercostal spaces. The signal was amplified and processed using a high differential amplifier with band pass filters set at 10 Hz and 2000 Hz (1902, Cambridge Electronic Design, Cambridge, UK). Additional analogue 50 Hz notch filter and AC coupling were used. Amplified signals were passed to an analogue to digital convertor (Powerlab, ADInstruments, Chalgrove, UK) and passed to a personal computer. Further digital filtering occurred at 20 Hz after data acquisition (LabChart v7.1, ADInstruments, Chalgrove, UK). $EMG_{para}$ recordings were performed with the patient relaxed in a chair or semi-recumbent in bed with arms supported. $EMG_{para}$ signals were acquired during resting breathing for at least 5 minutes and until more than 2 minutes of stable breathing were recorded. Repeat sniff manoeuvres were then performed with verbal encouragement until a consistent $EMG_{para}$ signal was recorded which was subsequently used as the maximum $EMG_{para}$ measurement. $EMG_{para}$ signals were analysed using the root mean squared (RMS) of the raw $EMG_{para}$ signal with a 40 ms moving window and normalised to the maximum RMS $EMG_{para}$ value ($EMG_{para\ \%\ max}$) analogous to the algorithm previously described for the analysis of $EMG_{di}$ (Jolley et al. (2009)). Whilst $EMG_{para\ \%\ max}$ reflects neural drive per breath and has been used in stable patients, here a neural respiratory drive index (NRDI, arbitrary units—AU) that incorporated respiratory rate to develop a measurement of neural drive to the respiratory muscles per unit time was used.

Results $EMG_{para}$ Reproducibility in Healthy Subjects

Ten healthy subjects had a mean age of 28±5.0 years (range 20-36 years), 60% male. The mean $EMG_{para}$ on visit 1 was 4.43±2.09 µV and on visit 2 was 4.15±2.01 µV with a co-efficient of variation (Cv) between visits of 0.10±0.08.

Figure 10A:
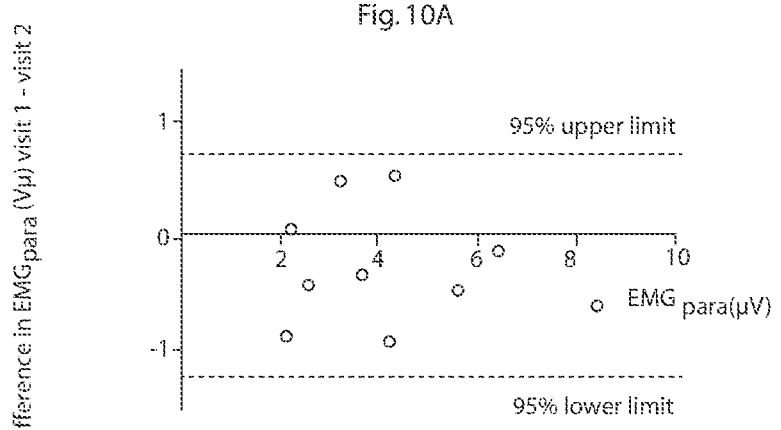
FIGS. 10A and 10B show Bland-Altman analysis of $EMG_{para}$ measured in healthy volunteers on two separate test days (A) with $EMG_{para}$ shown in μV with 95% upper and lower limits of agreement indicated and $EMG_{para\ \%\ max}$ (B) measured in stable COPD patients attending pulmonary rehabilitation on two separate occasions with $EMG_{para\ \%\ max}$ shown with 95% upper and lower limits of agreement.

The agreement between the first and second visit $EMG_{para}$ data, assessed using a Bland and Altman plot, is shown in FIG. 10A. The mean $EMG_{para}$ difference was −0.28±0.51 μV with limits of agreement of −1.28 and 0.73 μV. The mean $EMG_{para\ \%\ max}$ value on visit 1 was 2.74±2.53% and on visit 2 was 2.92±2.98% with a Cv of 0.37±0.27. The bias in $EMG_{para\ \%\ max}$ measurements from visit 1 to visit 2 was 0.18±1.68% within limits of agreement −3.12 to 3.47%. Pearson correlation coefficient showed strong correlation with both $EMG_{para}$ (r=0.97; p<0.001) and $EMG_{para\ \%\ max}$ (r=0.83; p=0.003).

$EMG_{para}$ Reproducibility in Stable COPD Patients

Figure 10B:
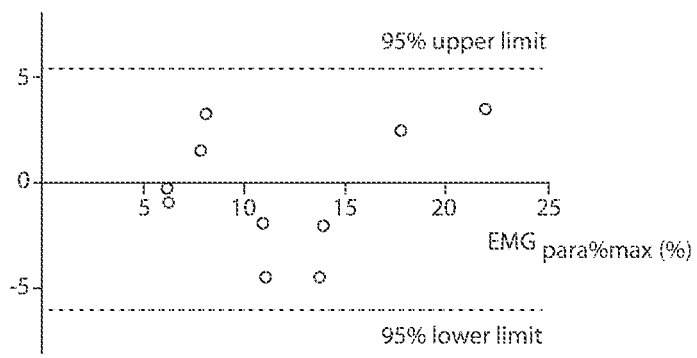

Ten patients with stable COPD were studied with a mean age 75±6.9 years (range 66-85 years), 50% male. Mean $FEV_1$ was 0.97±0.41 L. The mean $EMG_{para}$ on visit 1 was 8.83±5.29 μV and on visit 2 was 10.09±6.72 μV with a Cv of 0.19±0.13. The mean $EMG_{para}$ difference was 1.26±2.45 μV with limits of agreement of −3.54 and 6.06 mV. The mean $EMG_{para\ \%\ max}$ value on visit 1 was 11.59±5.70% and on visit 2 was 11.96±5.11% with a Cv of 0.15±0.09. The mean $EMG_{para\ \%\ max}$ difference was −0.37±2.93% with limits of agreement of −6.12 and 5.38%. A Bland-Altman plot of the first and second visit $EMG_{para\ \%\ max}$ data is shown in FIG. 10B. Regression analysis between visit 1 and visit 2 demonstrated a strong correlation with both $EMG_{para}$ (r=0.94; p<0.001) and $EMG_{para\ \%\ max}$ (r=0.89; p=0.002). No significant relationships could be identified between forced expiratory volume in 1 second ($FEV_1$) and either $EMG_{para}$ (p=0.78) or $EMG_{para\ \%\ max}$ (p=0.46) or the dyspnoea domain of the CRDQ and $EMG_{para}$ (p=0.17) or $EMG_{para\ \%\ max}$ (p=0.37).

Reproducibility of $EMG_{para}$ $EMG_{para}$ data is reported as root mean squared (RMS; μV). A representative trace of a patient with stable COPD during the sniff manoeuvres is shown in FIG. 11. Reproducibility of $EMG_{para}$ was confirmed in 10 healthy volunteers and 10 patients with stable COPD.

Example 2—EMGpara as a Physiological Biomarker to Monitor Change in AECOPD (to Predict Deterioration and Re-Admission)

Methods
Subjects

Patients with AECOPD were recruited. AECOPD was defined based on clinical features and basic investigations. Initial patient management was according to standard local guidelines with oral corticosteroids, antibiotics and a combination metered-dose inhalers and nebulised bronchodilators. The first $EMG_{para}$ measurement recorded within 24 hours of hospital arrival. Repeat $EMG_{para}$ measurements and the clinical dataset were recorded daily until the patient was reported as stable and suitable for hospital discharge.

Baseline Data

Demographic and anthropometric data were collected. Borg (Borg (1982) *Med. Sci. Sports Exerc.* 14, 377-81) and MRC dyspnoea score (Mahler et al. (1987) *Am. Rev. Respir. Dis.* 135, 1229-33; Celli et al. (2004) *N. Engl. J. Med.* 350, 1005-12) were used to assess subjective breathlessness. HRQL data was obtained using the Chronic Respiratory Disease Questionnaire (CRDQ). (Guyatt et al. (1987) *Thorax.* 42, 773-8). Spirometry was performed with a handheld device (EasyOne Diagnostic Spirometer, ndd Medical Technologies, Switzerland) according to standard guidelines (Quanjer et al. (1993) *Eur. Respir. J. Suppl.* 16, 5-40; Statement of the American Thoracic Society (1987) *Am. Rev. Respir. Dis.* 136; 1285-98). Repeat measurements were taken during admission. The patient was seated and rested for at least 5 minutes; bronchodilator therapy was withheld for the previous 4 hours. Heart rate (HR), oxygen saturations ($S_pO_2$) and respiratory rate (RR) were measured over one minute. Clinical data (HR, $S_pO_2$, RR, temperature (T), blood pressure (BP) and medical early warning score (MEWS) (Subbe et al. (2001) QJM. 94, 521-26) and the supervising senior clinician's summary opinion on clinical course were recorded from the medical notes and observation charts. A patient was defined as a clinical 'deteriorator' or 'improver' based on the summary opinion of the senior attending respiratory physician (respiratory specialist registrar or consultant) and the requirement for increased treatment. The respiratory clinicians were blinded to the $EMG_{para}$ measurement, which was analysed off line following patient discharge. $EMG_{para}$ signals were acquired either in a chair or semi-recumbent in bed. Oxygen therapy was only used when the $S_pO_2$ was ≤88%.

$EMG_{para}$ Measurement

The second intercostal space was identified using surface bony landmarks and the skin was prepared prior to placement of electrodes. $EMG_{para}$ signal acquisition and processing was analogous to the method described previously for $EMG_{di}$ as described above for with respect to Example 1. The resting signal was normalised to the maximum value obtained from a reproducible maximum sniff manoeuvre to produce the $EMG_{para\ \%\ max}$. To reflect changes in respiratory pattern, the product of $EMG_{para\ \%\ max}$ and respiratory rate was calculated to produce the neural respiratory drive index (NRDI; arbitrary units AU). Nasal cannulae connected to a differential pressure transducer (Validyne DP45, Validyne, Northridge, Calif., US) identified inspiratory and expiratory phases of breathing.

Data Analysis and Statistics

Reproducibility was assessed using co-efficient of variability and Bland-Altman analysis (Bland & Altman (1986) *Lancet* 327, 307-10). Relationships between $EMG_{para}$, $EMG_{para\ \%\ max}$ and NRDI and lung function parameters and HRQL data were analysed using regression analysis. Data were analysed using independent or paired t-test where appropriate. Data that were not normally distributed, as defined by the Kolmogorov-Smirnov test, were transformed and then analysed as parametric data or if the logarithm of the data remained non-normal then a non-parametric equivalent was used. Data analysis was conducted using SPSS software (SPSS, Chicago, Ill., USA). All data are presented as mean±SD, unless otherwise stated with a p value <0.05 considered as statistically significant.

Results

Change in $EMG_{para}$ in Patients with AECOPD 30 patients were recruited with a mean age of 72±10 years (47% male). On admission, the median MRC dyspnoea score was 5 (2-5). The median previous admission frequency and length of stay was 3 admissions (0-13) and 6 days (2-34), respectively. Baseline data is provided in Table 1 and full details can be found in Table 2.

TABLE 1

Standard Clinical Parameters and Indices of Neural Respiratory Drive on Admission

|  | Emergency Department | Baseline Measurements |
|---|---|---|
| MEWS | 3 (0-7) | 2 (0-4) |
| $FEV_1$ (L) | — | 0.60 ± 1.65 |
| FVC (L) | — | 1.53 ± 0.82 |
| $P_aO_2$ (kPa) | 10.0 ± 3.5 | — |
| $P_aCO_2$ (kPa) | 6.3 ± 1.4 | — |
| $EMG_{para\%max}$ (%) | — | 20.3 ± 9.9 |
| NRDI (AU) | — | 455 ± 263 |

Data presented as median (range) and mean ± standard devation;
MEWS = medical early warning score;
$FEV_1$ = forced expiratory volume in 1 second;
$P_aO_2$ = arterial partial pressure of oxygen;
$P_aCO_2$ = arterial partial pressure of carbon dioxide;

Changes in $EMG_{sc}$ in Patients with AECOPD

Baseline $EMG_{sc\,\%\,max}$ was 13.4±8.5% with no statistically significant changes occurring during the first 24 hours of admission in either improvers or deteriorators. There were no significant relationships between $EMG_{sc\,\%\,max}$ and other markers of NRD, measures of dyspnoea, spirometric measures or in the standard clinical variables.

Changes in NRD During Hospital Admission

Figure 12A:
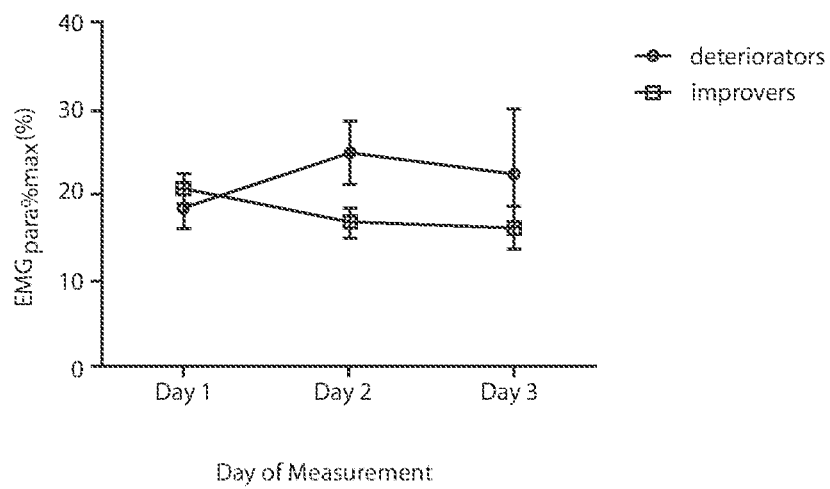
FIGS. 12A and 12 B show changes in NRD during hospital admission.
Figure 12B:
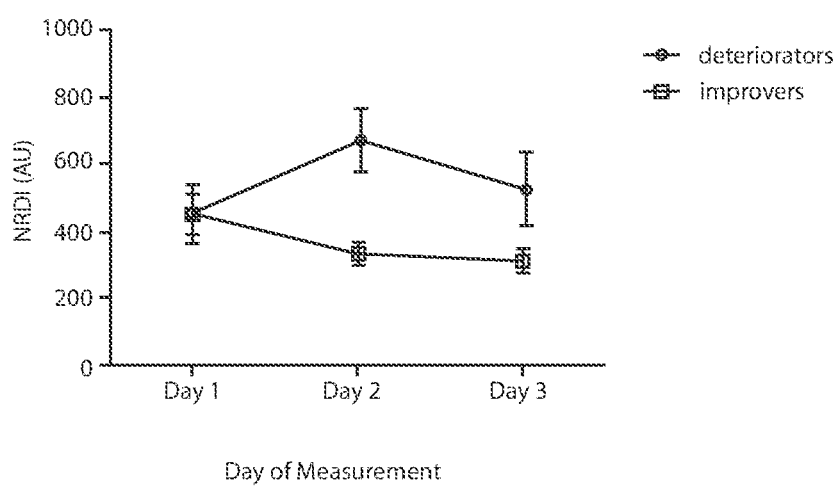
Figure 13A:
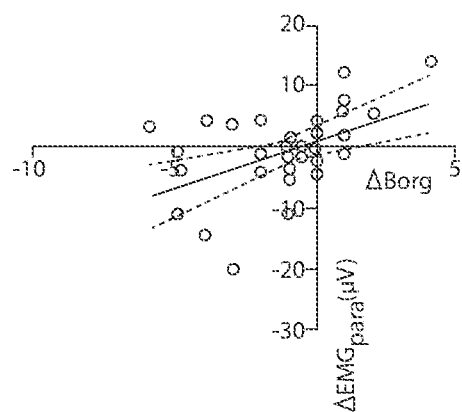
FIGS. 13A-13D compare ΔBorg score with $\Delta EMG_{para}$, $\Delta EMG_{para\ \%\ max}$, ΔNRDI and $\Delta FEV_1$.
Figure 13B:
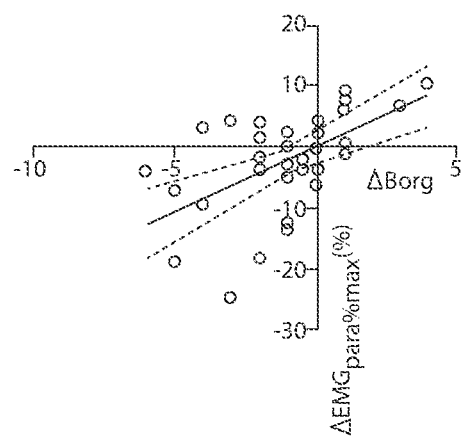
Figure 13C:
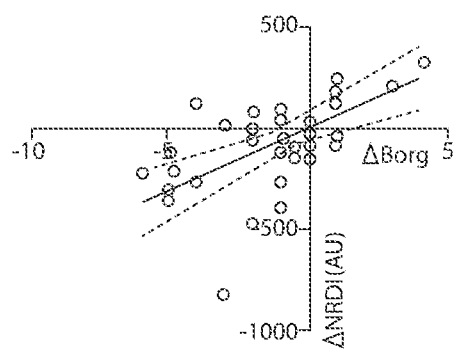
Figure 13D:
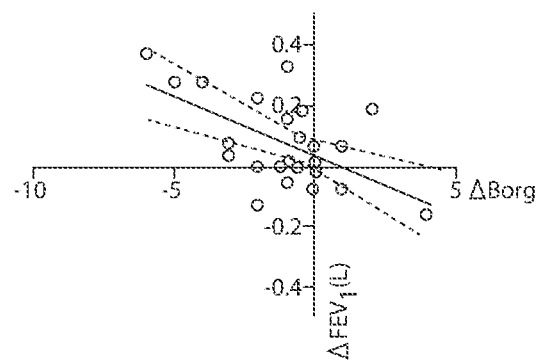

Both 'improvers' and 'deteriorators' had similar levels of NRD at initial reading that were significantly different at the follow up reading 24 hours later (mean difference $EMG_{para\,\%\,max}$=8.1, 95% Cl 0.2-16.0, p=0.046; mean difference NRDI=335, 95% Cl 163-507, p<0.001). Differences in NRD did not persist in subsequent measurements (FIG. 12).

TABLE 2

Baseline data of patients with AECOPD

|  | Age (years) | Sex (M/F) | $EMG_{para}$ (µV) | $EMG_{para\,\%\,max}$ (%) | NRDI (AU) | MEWS | Borg | RR (bpm) | $FEV_1$ (L) |
|---|---|---|---|---|---|---|---|---|---|
| 1 | 64 | F | 12.6 | 9.1 | 238 | 3 | 4 | 26 | UTP |
| 2 | 73 | F | 8.4 | 12.9 | 271 | 2 | 1 | 21 | 0.32 |
| 3 | 57 | M | 40.0 | 25.0 | 799 | 3 | 4 | 32 | UTP |
| 4 | 70 | F | 43.1 | 52.1 | 1512 | 4 | 7 | 29 | 0.52 |
| 5 | 72 | M | 7.5 | 11.0 | 221 | 1 | 3 | 20 | 1.64 |
| 6 | 72 | F | 5.8 | 21.0 | 543 | 3 | 6 | 26 | UTP |
| 7 | 77 | M | 3.7 | 11.5 | 298 | 2 | 7 | 26 | 0.49 |
| 8 | 81 | F | 14.0 | 21.2 | 509 | 2 | 6 | 24 | 0.46 |
| 9 | 68 | F | 22.4 | 20.3 | 406 | 1 | 4 | 20 | UTP |
| 10 | 64 | M | 16.8 | 25.3 | 506 | 1 | 7 | 20 | 0.69 |
| 11 | 80 | F | 6.5 | 13.9 | 291 | 4 | 3 | 21 | 0.58 |
| 12 | 74 | F | 9.2 | 14.8 | 355 | 2 | 2 | 24 | 0.45 |
| 13 | 69 | F | 18.6 | 16.0 | 383 | 2 | 8 | 24 | 0.49 |
| 14 | 89 | F | 21.8 | 36.7 | 808 | 2 | 1 | 22 | 0.24 |
| 15 | 90 | M | 8.3 | 14.0 | 252 | 1 | 0.5 | 18 | 0.69 |
| 16 | 79 | M | 6.4 | 16.9 | 422 | 3 | 5 | 25 | 0.48 |
| 17 | 85 | F | 7.5 | 16.2 | 390 | 3 | 7 | 24 | 0.53 |
| 18 | 72 | F | 16.4 | 10.4 | 249 | 2 | 4 | 24 | UTP |
| 19 | 72 | F | 9.5 | 12.2 | 231 | 1 | 5 | 19 | 0.62 |
| 20 | 75 | F | 19.8 | 15.7 | 378 | 4 | 8 | 24 | 0.44 |
| 21 | 63 | F | 18.4 | 28.1 | 534 | 1 | 8 | 19 | 0.6 |
| 22 | 72 | M | 20.9 | 32.3 | 550 | 1 | 3 | 17 | 0.67 |
| 23 | 75 | F | 16.3 | 36.7 | 770 | 3 | 4 | 21 | 0.34 |

TABLE 2-continued

Baseline data of patients with AECOPD

|  | Age (years) | Sex (M/F) | $EMG_{para}$ (μV) | $EMG_{para\ \%\ max}$ (%) | NRDI (AU) | MEWS | Borg | RR (bpm) | $FEV_1$ (L) |
|---|---|---|---|---|---|---|---|---|---|
| 24 | 83 | M | 15.7 | 17.9 | 287 | 0 | 0 | 16 | 1.58 |
| 25 | 43 | M | 13.3 | 21.0 | 440 | 2 | 3 | 21 | 0.5 |
| 26 | 64 | M | 17.4 | 25.1 | 527 | 2 | 9 | 21 | 0.45 |
| 27 | 62 | M | 16.7 | 29.7 | 594 | 2 | 3 | 20 | 0.58 |
| 28 | 85 | M | 6.2 | 13.2 | 304 | 2 | 3 | 23 | 0.82 |
| 29 | 63 | M | 3.0 | 8.0 | 144 | 1 | 5 | 18 | 2.11 |
| 30 | 80 | M | 10.5 | 21.3 | 426 | 1 | 9 | 20 | 0.96 |
| Mean ± SD | 72 ± 10 |  | 14.6 ± 9.3 | 20.32 ± 9.85 | 455 ± 263 | 2 (0-4)* | 4 (0-9)* | 22 ± 4 | 0.60 ± 1.65 |

*median (range)
Abbreviations:
UTP = patient unable to perform;
MEWS = medical early warning score;
$FEV_1$ = forced expiratory volume in 1 second Three patients received non-invasive ventilation with all cases initiated in the first 4 hours of admission in the emergency department. Nine patients were discharged with home oxygen, all were previously prescribed long term oxygen therapy.

Twenty-four patients had recordings on two occasions, five patients had recordings on three occasions and one patient had recordings on four occasions, producing 37 data pairs. ΔBorg score had a significant relationship with $\Delta EMG_{para}$ (r=+0.50; p=0.001), $\Delta EMG_{para\ \%\ max}$ (r=+0.57; p<0.001) and ΔNRDI (r=+0.60; p<0.001) as shown in FIG. 13 and $\Delta FEV_1$ (r=−0.58; p=0.002). There was no relationship observed with $\Delta S_pO_2$ (p=0.16) or ΔRR (p=0.08).

There were significant differences observed in mean change between 'improvers' and 'deteriorators' in all three $EMG_{para}$ indices. However, there were no significant between group differences in changes in RR, HR, $S_pO_2$ or $FEV_1$ (Table 3).

A significant (p=0.02), but clinically small (+0.5), difference was observed in MEWS between 'improvers' and 'deteriorators'. Patients who improved had statistically significant reduction in dyspnoea (ΔBorg −1.5; 95% CI −0.7--2.3), respiratory rate (ΔRR −1.8 bpm; 95% CI −0.2--3.3) and increase in FVC (ΔFVC 0.22 L; 95% CI 0.05-0.40), with no statistically significant differences demonstrable in physiological variables in the 'deteriorators'.

Figure 14A:
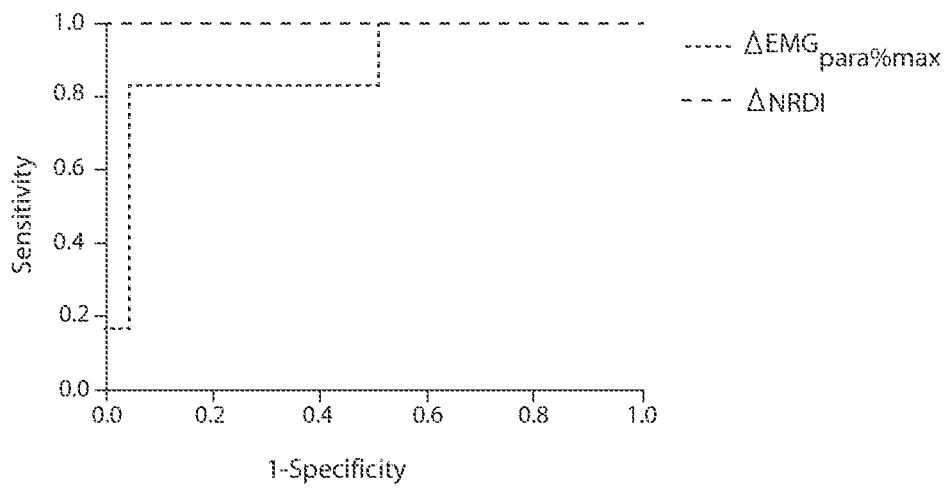
FIGS. 14A, 14B, 15A, and 15B show receiver operating characteristics plots.
Figure 14B:
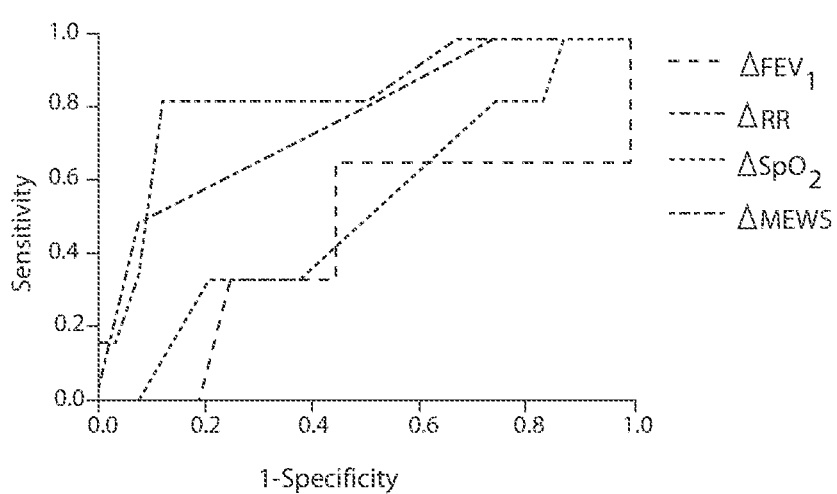

Receiver operating characteristics (ROC) plots (FIG. 14A) with change 'cut offs'>+6.6 for $EMG_{para\ \%\ max}$ and >+160 AU for NRDI had sensitivities of 83% (95% CI 54-100%) and 100% (95% CI 100-100%) and specificities of 96% (95% CI 88-100%) and 100% (95% CI 100-100%) for both $EMG_{para\ \%\ max}$ and NRDI, respectively. ROC plots of the standard clinical variables either did not statistically differ from the null hypothesis or could not produce a 'cut off' providing sensitivity >80% without reducing specificity to <90% (FIG. 14B).

Change in $EMG_{para}$ Between Admission and Discharge to Predict Readmission

A significant difference in $\Delta EMG_{para}$ and ΔNRDI between admission (1$^{st}$ measurement within 24 hours of admission) and discharge (final measurement within 24

TABLE 3

Difference between consecutive recordings of measured physiological variables in 30 patients from day of baseline measurement to repeat reading

|  | ΔMEWS* | ΔRR | $\Delta S_pO_2$ | $\Delta FEV_1$† | $\Delta EMG_{para}$ | $\Delta EMG_{para\ \%\ max}$ | ΔNRDI |
|---|---|---|---|---|---|---|---|
| 'Deteriorators' | 0.50 (0-1) | 4.5 ± 6.0 | 1.2 ± 2.4 | 0.03 ± 0.18 | 7.8 ± 4.9 | 6.2 ± 4.3 | 226 ± 58 |
| 'Improvers' | 0 (−2-1) | −1.8 ± 3.8 | 0.9 ± 2.7 | 0.06 ± 0.14 | −1.7 ± 5.5 | −3.5 ± 8.1 | −113 ± 221 |
| Mean difference |  | 6.3 | −0.6 | 0.03 | 9.6 | 9.6 | 339 |
| (95% CI) |  | (−0.1-12.6) | (−2.0-3.1) | (−0.42-0.36) | (4.4-14.8) | (4.5-14.8) | (234-444) |
| P value | 0.02 | 0.05 | 0.6 | 0.7 | 0.003 | 0.001 | <0.001 |

Data presented as mean ± standard deviation or *median (range);
†7 patients were unable to perform spirometry on 1 or more occasions, therefore analysis of $FEV_1$ was performed on 'improvers' n = 20 and 'deteriorators' n = 3.
MEWS = medical early warning score;
$FEV_1$ = forced expiratory volume in 1 second;
95% CI = 95% confidence intervals hours of clinical stability) was demonstrated between those patients readmitted within 14 days as a consequence of a respiratory deterioration and those patients who remained at home. However, ΔMEWS, $\Delta FEV_1$ and number of previous admissions did not differ between patients who were and were not readmitted (Table 4).

TABLE 4

Difference between admission and discharge of measured physiological variables in 30 patients either readmitted (n = 9) or not readmitted (n = 21) within 14 days of hospital discharge

|  | ΔMEWS* | ΔFEV₁† | Previous admissions* | ΔEMG$_{para\%max}$ | ΔNRDI |
|---|---|---|---|---|---|
| Readmitted | 0 (−1-2) | 0.09 ± 0.15 | 4 (0-14) | 1.98 ± 4.36 | 76 ± 134 |
| Not readmitted | 0 (−3-2) | 0.08 ± 0.10 | 3 (0-10) | −4.05 ± 10.30 | −127 ± 305 |
| Mean difference |  | 0.1 |  | 6.03 | 203 |
| (95% CI) |  | (0.14-0.11) |  | (11.5-0.54) | (39-366) |
| P value | 0.5 | 0.8 | 0.1 | 0.03 | 0.02 |

Figure 15A:
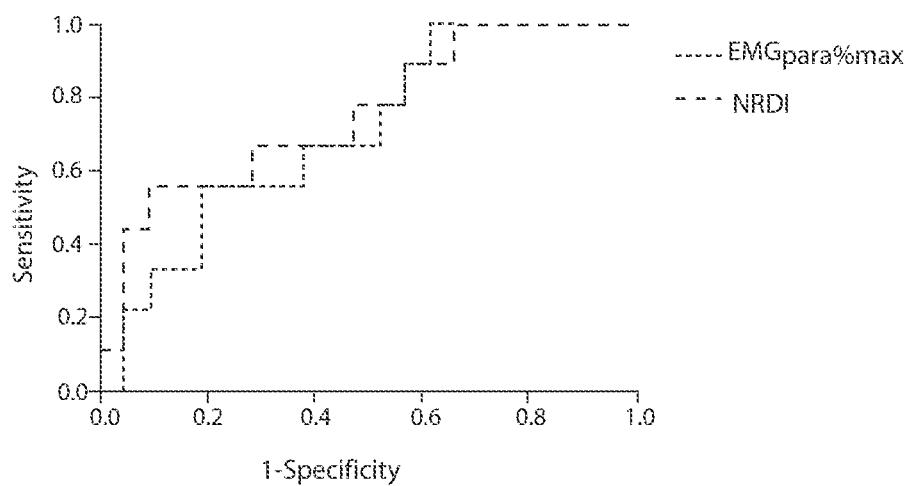
Figure 15B:
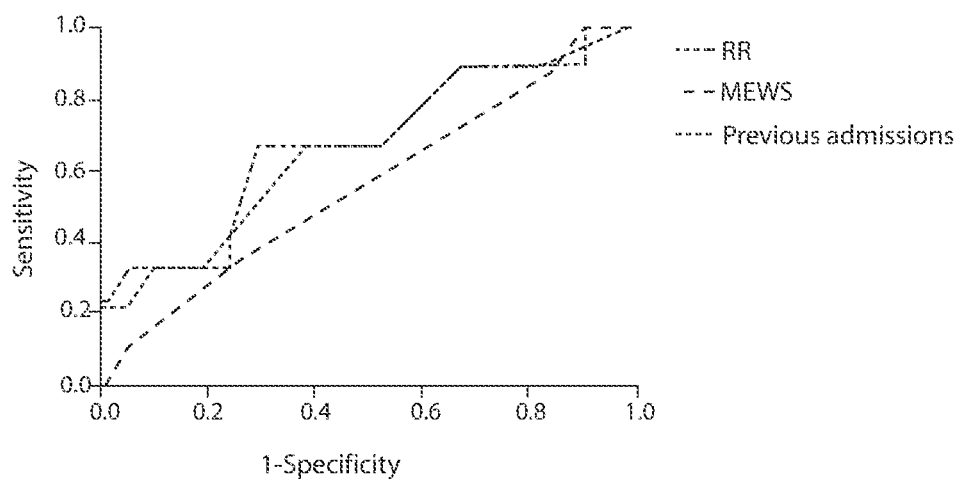

Data presented as mean ± standard deviation or * median (range);
†7 patients were unable to perform spirometry on 2 occasions, therefore analysis of FEV₁ was performed on readmitted n = 6, not readmitted n = 17.
MEWS = medical early warning score;
FEV₁ = forced expiratory volume in 1 second;
95% CI = 95% confidence intervals ROC plots (FIG. 15A) were calculated with 'cut offs' of a change in $EMG_{para\ \%\ max}$>0% and NRDI>50 AU during admission producing sensitivities of 67% (95% CI 36-97%) and 67% (95% CI 36-97%) and specificities of 62% (95% CI 41-83%) and 71% (95% CI 52-91%) for $EMG_{para\ \%\ max}$ and NRDI, respectively. None of the ROC plots for routine clinical variables differed significantly from the null hypothesis (FIG. 15B).

Discussion

Examples 1 and 2 demonstrate that $2^{nd}$ intercostal space (ICS) parasternal NRDI, calculated as a product of $EMG_{para}$ and RR normalised for maximum $EMG_{para}$, is a reproducible physiological biomarker in stable COPD patients and has greater sensitivity and specificity than standard clinical physiological parameters to identify AECOPD patients failing to respond to treatment. Furthermore, the failure of NRDI to fall during AECOPD requiring hospitalisation identifies patients who are more likely to be readmitted with a further respiratory deterioration.

Patient Selection

The AECOPD patients recruited were not consecutive admissions and therefore subject to selection bias. Despite this limitation, demographics and severity of patients were similar to previously reported data (Roberts et al. (2011) Thorax 66, 43-8). Furthermore, the goal of this study was to provide pilot data to demonstrate the feasibility and clinical usefulness of using non-invasive EMG monitoring as a physiological biomarker in the acute setting.

Surface EMG Para Measurement

Although the issues of surface EMG recording are well described (Luo et al. (2008) Clin. Sci. (Lond). 115, 233-44), contamination from other chest wall muscles cannot be excluded. Patient and electrode position during data acquisition were carefully observed to maximise the contribution of $2^{nd}$ ICS parasternal muscle to the inspiratory $EMG_{para}$ signal and minimising the non-respiratory muscle activity of other muscles. Needle electrode technique could be used to isolate parasternal muscle activity, but similar to oesophageal measurement of diaphragm electrical activity, this invasive technique is not suitable for the acute setting.

Validity and Reproducibility of $EMG_{para}$ $EMG_{para}$, as a measure of NRD, was shown to have satisfactory inter-occasion reproducibility in both healthy subjects and patients with stable COPD. Although the degree of variability with $EMG_{para}$ in COPD patients was greater in this study than that shown previously using $EMG_{di}$ (Jolley et al. (2009)) and $EMG_{para}$ in patients with cystic fibrosis (Reilly et al. (2011) Thorax 66, 240-46), the inter-occasion correlation for both healthy subjects and stable COPD was >0.80, which is a level that has previously been used to indicate acceptable inter-test agreement for surface electromyogram (Duiverman et al. (2004)).

Definition of Clinical Change

All patients met an event based criteria for a severe exacerbation of COPD requiring hospital admission (Anthonisen et al. (1987) Ann. Intern. Med. 106, 196-204; Trappenburg et al. (2011) Eur. Respir. J. 37, 1260-8). There is no 'gold standard' to predict or measure acute clinical progress in AECOPD (Trappenburg et al. (2011)), and therefore $EMG_{para}$ was compared to standard clinical parameters and the summary opinion of the supervising senior physician. Whilst this is a broad definition it is widely used in both research and clinical practice and is the benchmark by which other novel influential assessment tools have been judged (Leidy et al. (2011) Am. J. Respir. Crit. Care Med. 183, 323-9). Despite the limitations inherent with this choice of outcome it allows the data to be easily interpreted. Clinical gestalt is the interpretation and analysis by the physician of the patient's report of their clinical state as well as the findings from the physical examination incorporating standard physiological variables and clinical parameters, which are subsequently processed as part of learnt complex clinical algorithm to determine the clinical state of the patient and the response to treatment. In order to have measured the performance of this novel technique against a more definable objective marker the study population may have to be limited to those patients in respiratory failure. However, this would have limited the applicability of the study and would have been difficult to demonstrate that measures of NRD added to already established and widely available techniques to measure clinical progress in this group.

Significance of Findings

Parasternal Muscle Activity

Chest wall respiratory muscles have increased importance in patients with advanced COPD as progressive hyperinflation impacts adversely on diaphragm positioning and efficiency (Sharp et al. (1977) Am. Rev. Respir. Dis. 115, 47-56; Kyroussis et al. (2000) Eur. Respir. J. 15, 649-55), which results in a compensatory increase in chest wall and accessory respiratory muscle activity (Man et al. (2004) Thorax 59, 471-76). In particular, the uppermost parasternal intercostal muscles have been shown to be important inspiratory muscles (Legrand et al. (1996) J. Appl. Physiol. 80, 2097-101; De Troyer et al. (1996) J. Appl. Physiol. 80, 1490-4; De Troyer & Leduc (2006) J. Appl. Physiol. 101, 169-75).

Furthermore, these parasternals have minimal post-inspiratory activity (Easton et al. (1999) *J. Appl. Physiol.* 87, 1097-101) with the $2^{nd}$ ICS parasternal muscle demonstrating similar activity to the diaphragm (Gandevia et al. (2006) *J. Physiol.* 573; 263-75). However, during increasing hyperinflation, as observed during an AECOPD, the resting length of the parasternals is less affected than the diaphragm, such that the parasternals make a greater contribution to inspiratory pressure generation (Martinez et al. (1991) *Am. Rev. Respir. Dis.* 143; 476-480). This increase in parasternal activity is also associated with higher levels of dyspnoea (Ward et al. (1988) *J. Appl. Physiol.* 65, 2181-9). These data provide the scientific rationale to develop $EMG_{para}$ as a physiological biomarker to track changes in clinical state in patients with AECOPD. Patients failing to respond to therapy have persistent hyperinflation with sustained elevation in $EMG_{para}$ activity compared to those responding to therapy and associated respiratory muscle unloading which have a decline in $EMG_{para}$ activity as the lung volumes and diaphragm and parasternal activity return to baseline. Finally, NRD was expressed as a product of $EMG_{para}$ and RR normalised for maximum $EMG_{para}$ to produce NRDI, which incorporates the peak RMS inspiratory parasternal muscle activity per unit time as a ratio of maximum NRD.

Dyspnoea

Dyspnoea provides a significant symptom burden in COPD. An objective method of assessing the severity of breathlessness has previously been lacking, with clinicians using subjective assessment tools. Physiological indicators of disease severity in COPD, such as $FEV_1$, are acknowledged to be poorly predictive of dyspnoea (Mahler (1992) *Chest* 101, 242S-7S). In contrast, changes in NRD have been shown to explain variance in exercise induced dyspnea (Marin et al. (1999) *Chest* 115, 1293-300) The applicant observed a similar relationship between change in Borg score and change in $EMG_{para}$. Furthermore, as the initial measurements were recorded following commencement of emergency therapy, in some patients there were relatively small changes in $2^{nd}$ ICS parasternal muscle electrical activity and breathlessness, indicating that that this technique is sensitive enough to monitor relatively modest changes even after treatment initiation. These data, therefore, support the use of non-invasive $2^{nd}$ ICS parasternal electromyography as a physiological biomarker of NRD that reflects perception of dyspnoea severity during AECOPD. Furthermore, as $FEV_1$ has a weak relationship with dyspnoea, there is potential for $EMG_{para}$ to be applied to patients in the stable state to monitor progression of disease and detect exacerbation onset, although more work is required to fully elucidate this relationship.

Monitoring Response to Treatment

NRD was shown to monitor response to treatment in patients admitted with AECOPD when calculated as $EMG_{para\ \%\ max}$ and NRDI. The reproducibility data indicate that the 'cut off' chosen for maximum sensitivity and specificity of detection for clinical change ($EMG_{para\ \%\ max} > 6.6\%$) represents a genuine and detectable change in NRD as it is above the 95% upper limit of agreement on the Bland-Altman plot. In this population of AECOPD patients, this would have correctly tracked deterioration in 5 out of 6 occasions. This high sensitivity and specificity was further improved with the addition of respiratory rate to produce the NRDI, which correctly identified all episodes of deterioration in this sample set. This demonstrates the potential clinical utility of the test with the integrated physiological signal accurately reflecting the summary opinion of the senior attending respiratory physician in a way unable to be replicated by any of the standard clinical variables assessed.

Re-Admission

In addition to the ability to track changes in NRD during AECOPD using this technique, the applicant has also shown that failure of NRDI to fall in response to therapy identifies those patients who are likely to be readmitted within 14 days of discharge with a further respiratory deterioration. There has not previously been reported any clinically useful biomarker that can predict readmission in such patients (Cao et al. (2006) *Respirology* 11, 188-95). Previous data in COPD patients with severe disease, as indicated by an $FEV_1 < 1$ L at discharge or >2 previous admissions in the preceding 12 months, reported that these patients were more likely to be readmitted following an exacerbation of COPD (Garcia-Aymerich et al. (2003) *Thorax* 58, 100-105). The specificity of these particular predictors in the current cohort of patients was poor at <0.5 and therefore these are not clinically useful. Failure of NRDI to fall in response to treatment provides an easy to apply novel physiological biomarker to predict readmission in high risk patients. Data from the ECLIPSE study has suggested the 'frequent exacerbator' is a distinct phenotype in COPD (Hurst et al. (2010) *N. Engl. J. Med.* 363, 1128-38). The measurement of NRDI in this context is not simply acting as a measure of disease severity or to identify the frequent exacerbator phenotype, as if the analysis were limited to those patients with ≥2 previous admissions (n=22), the sensitivity and specificity to predict readmission at 14 days remained similar to the whole cohort at 63% and 64%, respectively. The ability of this physiological tool to maintain its sensitivity and specificity in the higher risk group of patients increases the clinical utility with the ability to further risk stratify the most high risk patients. With the increasing role of early discharge and COPD outreach schemes to support patients in the community, this technique could facilitate clinical selection to identify those patients that require greater community support or further hospital treatment prior to discharge. This approach has increasing importance as the rising incidence of failed hospital discharge have been highlighted by the UK government as an area for improved performance with potential financial penalties for hospitals.

The Examples set out below illustrate various situations, measurements taken and expected outcomes.

Example 3

4.1 Patient 1

Scenario: Neural respiratory drive falls between hospital admission and discharge Outcome: The patient did not require re-admission to hospital within 28 days.

TABLE 5

| Trace | RR | Mean (peakEMG$_{para}$ 30) | EMG$_{para\%max}$ | NRDI | maxEMG$_{para}$ |
| --- | --- | --- | --- | --- | --- |
| Admission | 21 | 31.41 | 23.10 | 485.13 | 135.95 |
| Discharge | 20 | 9.01 | 6.98 | 139.67 | 129.01 |

Figure 16:
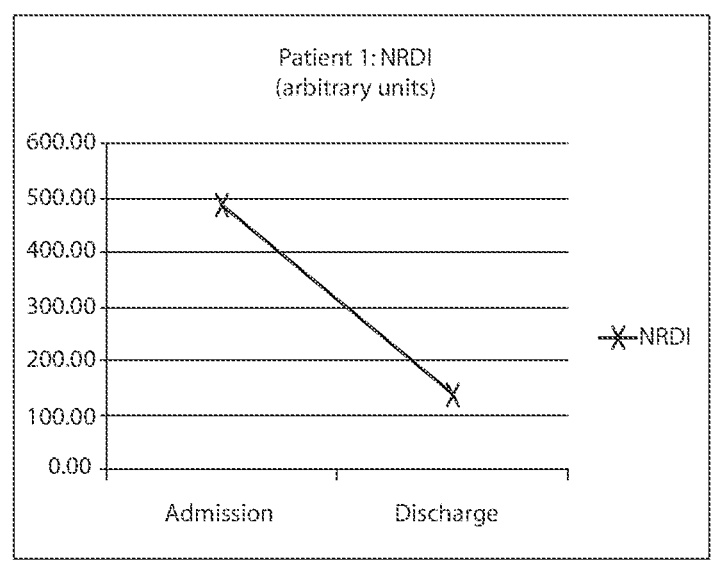
FIGS. 16, 17, and 18 depict measurements taken and expected outcomes for patients 1, 2, and 3, respectively.

Data are depicted in FIG. 16.

Example 4

Scenario: Neural respiratory drive rises between hospital admission and discharge Outcome: The patient required re-admission to hospital within 28 days

TABLE 6

| Trace | RR | Mean (peakEMG$_{para}$ 30) | EMG$_{para\%max}$ | NRDI | maxEMG$_{para}$ |
|---|---|---|---|---|---|
| Admission | 23 | 21.00 | 28.01 | 644.24 | 74.98 |
| Discharge | 28 | 25.10 | 38.94 | 1090.37 | 64.45 |

Figure 17:
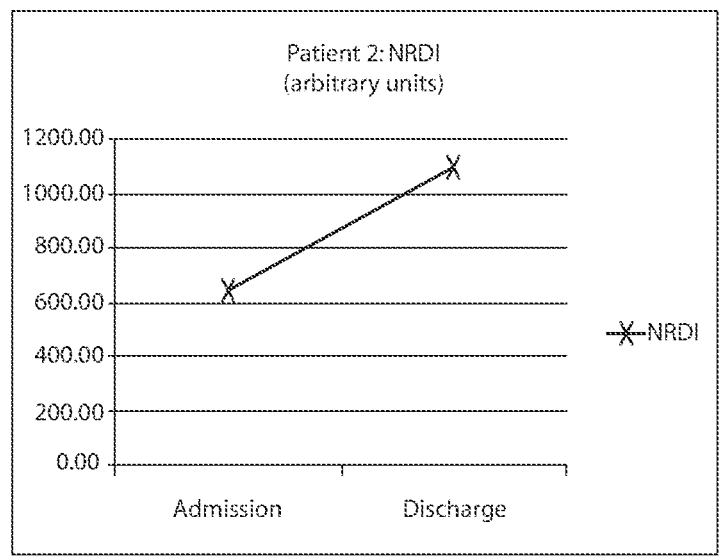

Data are depicted in FIG. 17.

Example 5

Scenario: Neural respiratory drive rises significantly during hospital admission as clinical respiratory status declines due to treatment failure, i.e., monitoring acute deterioration Outcome: Escalation in medical treatment above standard initial therapy

TABLE 7

| Trace | RR | Mean (peakEMG$_{para}$ 30) | EMG$_{para\%max}$ | NRDI | maxEMG$_{para}$ |
|---|---|---|---|---|---|
| 1 | 16 | 11.81 | 16.24 | 259.90 | 72.72 |
| 2 | 22 | 12.83 | 21.76 | 478.76 | 58.95 |
| 3 | 25 | 14.28 | 16.72 | 418.12 | 85.38 |
| 4 | 18 | 9.02 | 8.51 | 153.23 | 105.98 |

Figure 18:
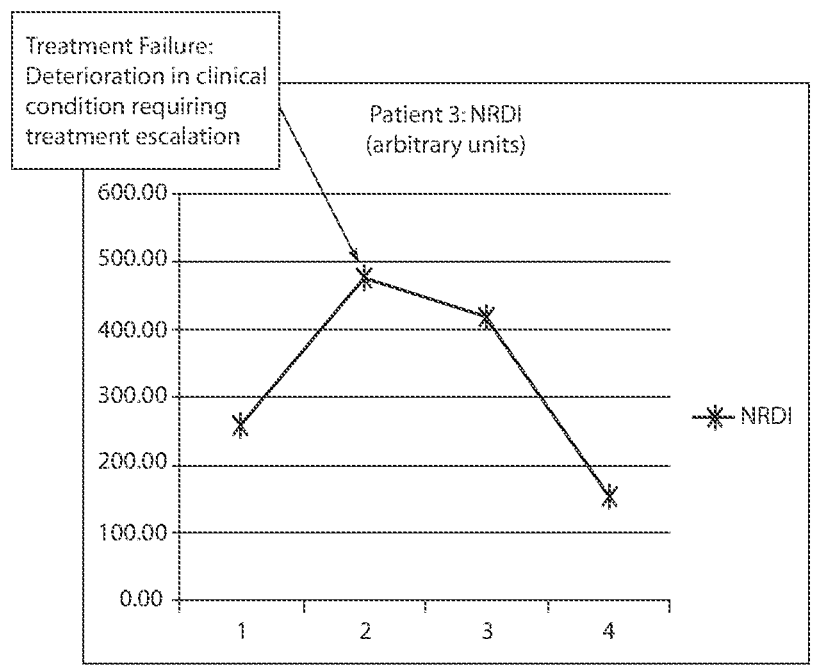

Data are depicted in FIG. 18.

The skilled person will appreciate that the above description and Examples are exemplary only and modifications may be made thereto.

What is claimed is:

1. A method of monitoring a patient having a respiratory disease, the method including the steps of:
   measuring neural respiratory drive using a monitoring device by:
   (1) recording a parasternal electromyogram (EMG$_{para}$) signal during resting breathing and a maximal parasternal electromyogram (EMG$_{paramax}$) signal during a maximum sniff manoeuvre
   (2) obtaining a root mean square of the EMG$_{para}$ signal to obtain a first rectified parasternal trace, the first rectified parasternal trace having an area thereunder;
   (3) obtaining a root mean square of the EMG$_{paramax}$ signal to obtain a second rectified parasternal trace, the second rectified parasternal trace having an area thereunder;
   (4) calculating a normalized neural respiratory drive by expressing a peak EMG$_{para}$ signal determined from the first rectified parasternal trace obtained in Step 2 as a percentage of a peak EMG$_{paramax}$ signal determined from the second rectified parasternal trace obtained in Step 3;
   (5) obtaining a respiratory rate of the patient, expressed as breaths per minute;
   (6) obtaining a value for a neural respiratory drive index by multiplying a value of the normalized neural respiratory drive obtained in Step 4 by the respiratory rate;
   (7) measuring the area under the first rectified parasternal trace to obtain a value for resting neural respiratory drive time product;
   (8) obtaining a normalized value for neural respiratory drive time index as a percentage by multiplying the value for the resting neural respiratory drive time product by the respiratory rate and dividing by a maximum area under the curve of the second rectified parasternal trace;
   (9) repeating Steps (1) through (8) continuously and/or after a first given period of time; and
   (10) comparing two neural respiratory drive index values obtained and comparing two neural respiratory drive time index values obtained in order to predict treatment failure and/or clinical deterioration and/or admission from home or re-admission to hospital.

2. A method as claimed in claim 1, wherein Steps 1 to 8 are carried out upon admission into hospital and repeated just prior to discharge from hospital.

3. A method as claimed in claim 1, wherein the respiratory disease is:
   (1) an acute exacerbation of chronic obstructive pulmonary disease;
   (2) an acute exacerbation of chronic respiratory disease;
   (3) acute respiratory failure;
   (4) chronic respiratory disease;
   (5) chronic respiratory failure;
   (6) acute exacerbation of chronic heart failure;
   (7) acute heart failure; or
   (8) chronic heart failure.

4. A method as claimed in claim 1, wherein the peak EMG$_{para}$ signal is obtained for each inspiration over a time period of 30 seconds to 3 minutes.

5. A method as claimed in claim 1, wherein the step of measuring the neural respiratory drive using the monitoring device is performed in real time, wherein the EMG$_{para}$ signal and the EMG$_{paramax}$ signal are acquired from surface electrodes, and wherein the respiratory rate, the neural respiratory drive, and the neural respiratory drive index are displayed on the monitoring device.

6. A method as claimed in claim 5, including displaying the neural respiratory drive time product and the neural respiratory drive time index on the monitoring device.

7. A method as claimed in claim 5, wherein the EMG$_{para}$ signal and the EMG$_{paramax}$ signal are from second intercostal parasternal muscles of the patient.

8. A method as claimed in claim 1, wherein the step of recording the EMG$_{para}$ signal and the EMG$_{paramax}$ signal includes:
   1. placing surface electrodes over parasternal muscles of a second intercostal space of the patient along with a reference electrode over an electrically neutral clavicle of the patient;
   2. amplifying electrical signals from the surface electrodes; and
   3. passing the amplified electrical signals to an analog to digital converter.

9. A method as claimed in claim 8, wherein amplifying the electrical signals includes amplifying by a factor of 1000 and analog filtering at 10 Hz and 2000 Hz to remove contributions from other muscle activity.

10. A method as claimed in claim 1, including at least one of the following features:
    signal quality assessment;
    electrocardiogram (ECG) detection and heart rate calculation; and
    ECG artifact accommodation or removal from the EMG$_{para}$ signal.

11. A method as claimed in claim 1, wherein the monitoring is continuous.

12. A method as claimed in claim 1, including obtaining an electrocardiography signal, and removing artifacts of the electrocardiography signal from a raw parasternal electromyography trace.

13. A method as claimed in claim 1, wherein the monitoring is carried out in real time.

14. A monitoring device including: a signal input, and a processing unit, the monitoring device being arranged to:
  (1) receive a parasternal electromyogram ($EMG_{para}$) signal obtained during resting breathing at the signal input;
  (2) receive a maximal parasternal electromyogram ($EMG_{paramax}$) signal obtained during at least two sniff maneuvers; and
  (3) execute computer program code in the processing unit to:
   (a) determine a root mean square of the $EMG_{para}$ signal to obtain a first rectified parasternal trace having an area thereunder;
   (b) determine a root mean square of the $EMG_{paramax}$ signal obtained at (2) to obtain a second rectified parasternal trace having an area thereunder;
   (c) express a peak value of the root mean square of the $EMG_{para}$ signal obtained at (1) as a percentage of a peak value of the root mean square of the $EMG_{para}$ signal obtained during the at least two sniff maneuvers at (2) to obtain a value for neural respiratory drive;
   (d) receive data on a respiratory rate of a patient, expressed as breaths per minute;
   (e) determine a value for a neural respiratory drive index by multiplying the value of the neural respiratory drive by the respiratory rate;
   (f) identify the area under the curve of the first rectified parasternal trace for each inspiration over a given period of time to obtain a resting neural respiratory drive time product;
   (g) calculate a mean of the area under the curves identified at (f);
   (h) determine a value for neural respiratory drive time index by multiplying the resting neural respiratory drive time product by the respiratory rate and dividing by a maximum area under the curve of the second rectified parasternal trace and
   (i) store the values of the neural respiratory drive index and the neural respiratory drive time index in a data repository.

15. A monitoring device as claimed in claim 14, being arranged to compare a subsequent neural respiratory drive index and a subsequent neural respiratory drive time index with the respective stored values.

16. A monitoring device as claimed in claim 14, wherein the device is arranged to receive and determine $EMG_{para}$ signals during at least three sniff maneuvers.

17. A monitoring device as claimed in claim 14, wherein the device is arranged to display the value of the neural respiratory drive in real time.

* * * * *

UNITED STATES PATENT AND TRADEMARK OFFICE
CERTIFICATE OF CORRECTION

PATENT NO. : 10,617,307 B2
APPLICATION NO. : 15/640049
DATED : April 14, 2020
INVENTOR(S) : Hart et al.

Page 1 of 1

It is certified that error appears in the above-identified patent and that said Letters Patent is hereby corrected as shown below:

On the Title Page

Item (73) Please remove the following as an Assignee:
KING'S COLLEGE LONDON, OF THE STRAND, London (GB)

Signed and Sealed this
Third Day of November, 2020

Andrei Iancu
*Director of the United States Patent and Trademark Office*